(12) United States Patent
Rottlander et al.

(10) Patent No.: US 7,368,472 B2
(45) Date of Patent: May 6, 2008

(54) 1,2,4-TRIAMINOBENZENE DERIVATIVES USEFUL FOR TREATING DISORDERS OF THE CENTRAL NERVOUS SYSTEM

(75) Inventors: Mario Rottlander, Greve (DK); Andreas Ritzen, Vanlose (DK); Morten Bang Norgaard, Lyngby (DK); Nikolay Khanzhin, Frederiksberg (DK); Christian Wenzel Tornoe, Kobenhavn S (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 120 days.

(21) Appl. No.: 10/540,075

(22) PCT Filed: Dec. 18, 2003

(86) PCT No.: PCT/DK03/00906

§ 371 (c)(1),
(2), (4) Date: Jun. 22, 2005

(87) PCT Pub. No.: WO2004/058739

PCT Pub. Date: Jul. 15, 2004

(65) Prior Publication Data

US 2006/0014822 A1    Jan. 19, 2006

Related U.S. Application Data

(60) Provisional application No. 60/436,697, filed on Dec. 27, 2002.

(30) Foreign Application Priority Data

Dec. 27, 2002  (DK) ................................ 2002 02012

(51) Int. Cl.
*A61K 31/38* (2006.01)
*C07D 333/12* (2006.01)

(52) U.S. Cl. ........................... 514/438; 549/74; 549/75

(58) Field of Classification Search .................. 549/74, 549/75; 514/445, 438
See application file for complete search history.

(56) References Cited

FOREIGN PATENT DOCUMENTS

| WO | WO 97/15300 | 5/1997 |
|----|-------------|--------|
| WO | WO 01/01970 | 1/2001 |
| WO | WO 01/22953 | 4/2001 |
| WO | WO 02/49628 | 6/2002 |

OTHER PUBLICATIONS

Khanzhin et al, CA 141:314020, 2004.*
Passmore et al., 2003, The Journal of Neuroscience, 23(18):7227 (i.e., abstract).*
Gribkoff, 2003, Expert Opin. Ther. Targets, 7(6):737 (i.e., abstract).*
Selkoe, 2001, Physiological Reviews, 2001, 81(2):741 (I.e., abstract).*
Wickenden, et al. "Retigabine, A Novel Anti-Convulsant, Enhances Activation of KCNQ2/Q3 Potassium Channels" Molecular Pharmacology, 2000, 58, 591-600.
Tober, et al. "D-23129: a potent anticonvulsant in the amygdala kindling model of complex partial seizures" European Journal of Pharmacology, 1996, 303, 163-169.
Wickenden, et al. "KCNQ Channel Expression in Rat DRG Following Nerve Ligation" Society for Neuroscience Abstracts, 2002, No. 454.7.
Goldstein, et al. "Localization of KCNQ and KCNE Channel Subunits in the Central and Peripheral Nervous System of the Rat" Society for Neuroscience Abstracts, 2003, No. 53.8.
Saganich, et al. "Differential Expression of Genes Encoding Sub-threshold-Operating Voltage-Gated K+ Channels in Brain" The Journal of Neuroscience, 2001, 21, 4609-4624.
Noda, et al. "KCN Channels in Glial Cells" Society for Neuroscience Abstracts, 2003, No. 53.9.

* cited by examiner

*Primary Examiner*—Rei-tsang Shiao
(74) *Attorney, Agent, or Firm*—Stephen G. Kalinchak

(57) ABSTRACT

The present invention concerns 1,2,4-triaminobenzene derivatives of the general formula I or pharmaceutically acceptable salts thereof and the use thereof.

20 Claims, No Drawings

1,2,4-TRIAMINOBENZENE DERIVATIVES USEFUL FOR TREATING DISORDERS OF THE CENTRAL NERVOUS SYSTEM

This application is a §371 national stage of PCT International Application No. PCT/DK2003/000906, filed Dec. 18, 2003 on behalf of H. Lundbeck A/S, which is a continuation-in-part of and claims the benefit of priority under 35 U.S.C. §119(e) of U.S. Provisional Application No. 60/436,697, filed Dec. 27, 2002 and claims the benefit of priority under 35 U.S.C. §119(a)-(d) of Danish Application No. PA200202012, filed Dec. 27, 2002, the contents of which are hereby incorporated by reference into the subject application.

FIELD OF THE INVENTION

The present invention relates to novel 1,2,4-triaminobenzene derivatives being openers of the KCNQ family potassium channels. The compounds are useful for the prevention, treatment and/or inhibition of disorders of the central nervous system.

BACKGROUND OF THE INVENTION

Ion channels are cellular proteins that regulate the flow of ions, including potassium, calcium, chloride and sodium into and out of cells. Such channels are present in all animal and human cells and affect a variety of processes including neuronal transmission, muscle contraction and cellular secretion.

Humans have over 70 potassium channel subunits (Jentsch *Nature Reviews Neuroscience* 2000, 1, 21-30) with a great diversity with regard to both structure and function. Neuronal potassium channels, which are found in the brain, are primarily responsible for maintaining a negative resting membrane potential, as well as controlling membrane repolarisation following an action potential.

One subset of potassium channel genes is the KCNQ family. Mutations in four out of five KCNQ genes have been shown to underlie diseases including cardiac arrhythmnias, deafness and epilepsy (Jentsch *Nature Reviews Neuroscience* 2000, 1, 21-30).

The KCNQ4 gene is thought to encode the molecular correlate of potassium channels found in outer hair cells of the cochlea and in Type I hair cells of the vestibular apparatus, mutations in which lead to a form of inherited deafness.

KCNQ1 (KvLQT1) is co-assembled with the product of the KCNE1 (minimal K(+)-channel protein) gene in the heart to form a cardiac-delayed rectifier-like K(+) current. Mutations in this channel can cause one form of inherited long QT syndrome type 1 (LQT1), as well as being associated with a form of deafness (Robbins *Pharmacol Ther* 2001, 90, 1-19).

The genes KCNQ2 and KCNQ3 were discovered in 1988 and appear to be mutated in an inherited form of epilepsy known as benign familial neonatal convulsions (Rogawski *Trends in Neurosciences* 2000, 23, 393-398). The proteins encoded by the KCNQ2 and KCNQ3 genes are localised in the pyramidal neurons of the human cortex and hippocampus, regions of the brain associated with seizure generation and propagation (Cooper et al. *Proceedings National Academy of Science USA* 2000, 97, 4914-4919).

KCNQ2 and KCNQ3 are two potassium channel subunits that form "M-currents" when expressed in vitro. The M-current is a non-inactivating potassium current found in many neuronal cell types. In each cell type, it is dominant in controlling membrane excitability by being the only sustained current in the range of action potential initiation (Marrion *Annual Review Physiology* 1997, 59, 483-504). Modulation of the M-current has dramatic effects on neuronal excitability, for example, activation of the current will reduce neuronal excitability. Thus, openers of these KCNQ channels will reduce excessive neuronal activity in conditions such as seizures and diseases characterised by excessive neuronal activity such as epilepsy and neuropathic pain.

Retigabine (D-23129; N-(2-amino-4-(4-fluorobenzylamino)-phenyl) carbamic acid ethyl ester) and analogues thereof are disclosed in EP554543. Retigabine is an anti-convulsive compound with a broad spectrum and potent anticonvulsant properties, both in vitro and in vivo. It is active after oral and intraperitoneal administration in rats and mice in a range of anticonvulsant tests including: electrically induced seizures, seizures induced chemically by pentylenetetrazole, picrotoxin and N-methyl-D-aspartate (NMDA) and in a genetic animal model, the DBA/2 mouse (Rostock et al. *Epilepsy Research* 1996, 23, 211-223). In addition, retigabine is active in the amygdala kindling model of complex partial seizures, further indicating that this compound has potential for anti-convulsive therapy. In clinical trials, retigabine has recently shown effectiveness in reducing the incidence of seizures in epileptic patients (Bialer et al. *Epilepsy Research* 2002, 51, 31-71).

Retigabine has been shown to activate a K(+) current in neuronal cells and the pharmacology of this induced current displays concordance with the published pharmacology of the M-channel, which recently was correlated to the KCNQ2/3 K(+) channel heteromultimer. This suggests that activation of KCNQ2/3 channels may be responsible for some of the anticonvulsant activity of this agent (Wickenden et al. *Molecular Pharmacology* 2000, 58, 591-600)—and that other agents working by the same mechanism may have similar uses.

KCNQ 2 and 3 channels have been reported to be upregulated in models of neuropathic pain (Wickenden et al. *Society for Neuroscience Abstracts* 2002, 454.7), and potassium channel modulators have been hypothesised to be active in both neuropathic pain and epilepsy (Schroder et al. *Neuropharmacology* 2001, 40, 888-898; Blackburn-Munro and Jensen *European Journal of Pharmacology* 2003, 460, 109-116). Furthermore, the localisation of KCNQ channel mRNA is reported in brain and other central nervous system areas associated with pain (Goldstein et al. *Society for Neuroscience Abstracts* 2003, 53.8).

In addition to a role in neuropathic pain, the expression of mRNA for KCNQ 2-5 in the trigeminal and dorsal root ganglia and in the trigeminal nucleus caudalis implies that openers of these channels may also affect the sensory processing of migraine pain (Goldstein et al. *Society for Neuroscience Abstracts* 2003, 53.8).

Recent reports demonstrate that mRNA for KCNQ 3 and 5, in addition to that for KCNQ2, are expressed in astrocytes and glial cells. Thus KCNQ 2, 3 and 5 channels may help modulate synaptic activity in the CNS and contribute to the neuroprotective effects of KCNQ channel openers (Noda et al., *Society for Neuroscience Abstracts* 2003, 53.9). Retigabine and other KCNQ modulators may thus exhibit protection against the neurodegenerative aspects of epilepsy, as retigabine has been shown to prevent limbic neurodegeneration and the expression of markers of apoptosis following kainic acid-induced status epilepticus in the rat (Ebert et al. *Epilepsia* 2002, 43 Suppl 5, 86-95). This may have relevance for preventing the progression of epilepsy in patients, i.e. be anti-epileptogenic. Retigabine has also been shown to delay the progression of hippocampal kindling in the rat, a further model of epilepsy development (Tober et al. *European Journal Of Pharmacology* 1996, 303, 163-169).

Given that anticonvulsant compounds such as benzodiazepines and chlormethiazole are used clincially in the treatment of the ethanol withdrawal syndrome and that other anticonvulsant compounds e.g. gabapentin, are very effective in animal models of this syndrome (Watson et al. *Neuropharmacology* 1997, 36, 1369-1375), we expect that other anticonvulsant compounds such as KCNQ openers will also be effective in this condition.

mRNA for KCNQ 2 and 3 subunits are found in brain regions associated with anxiety and emotional behaviours such as bipolar disorder e.g. hippocampus and amygdala (Saganich et al. *Journal of Neuroscience* 2001, 21, 4609-4624), and retigabine is reportedly active in some animal models of anxiety-like behaviour (Hartz et al. *Journal of Psychopharmacology* 2003, 17 suppl 3, A28, B16), and other clinically used anticonvulsant compounds are used in the treatment of bipolar disorder.

WO 200196540 discloses the use of modulators of the M-current formed by expression of KCNQ2 and KCNQ3 genes for insomnia, whilst WO 2001092526 discloses that modulators of KCNQ5 can be utilized for the treatment of sleep disorders.

WO01/022953 describes the use of retigabine for prophylaxis and treatment of neuropathic pain such as allodynia, hyperalgesic pain, phantom pain, neuropathic pain related to diabetic neuropathy and neuropathic pain related to migraine.

WO02/049628 describes the use of retigabine for the prevention, treatment, inhibition and amelioration of anxiety disorders such as anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia and specific phobias.

WO97/15300 describes the use of retigabine for the treatment of neurodegenerative disorders such as Alzheimer's disease, Huntington's chorea, multiple sclerosis, amyotrophic lateral sclerosis, AIDS-induced encephalopathy and other infection-related encephalopathies being caused by rubella viruses, herpes viruses, borrelia and by unknown pathogens, Creutzfeld-Jakob disease, Parkinson's disease, trauma-induced neurodegenerations, and neuronal hyperexcitation states such as in medicament withdrawal or by intoxication, neurodegenerative disorders of the peripheral nervous system such as polyneuropathies and polyneuritides.

Hence, there is a great desire for novel compounds, which are potent openers of the KCNQ family potassium channels.

Also desired are novel compounds with improved properties relative to known compounds, which are openers of the KCNQ family potassium channels, such as retigabine. Improvement of one or more of the following parameters is desired: half-life, clearance, selectivity, interactions with other medications, bioavailability, potency, formulability, chemical stability, metabolic stability, membrane permeability, solubility and therapeutic index. The improvement of such parameters may lead to improvements such as:

an improved dosing regime by reducing the number of required doses a day,
ease of administration to patients on multiple medications
reduced side effects,
enlarged therapeutic index,
improved tolerability and/or
improved compliance.

SUMMARY OF THE INVENTION

Accordingly, one object of the present invention is to provide novel compounds, which are potent openers of the KCNQ family potassium channels.

The compounds of the invention are 1,2,4-triaminobenzene derivatives of the general formula I or pharmaceutically acceptable salts thereof

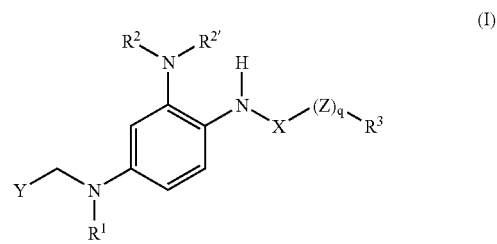

wherein
$R^1$, $R^2$, $R^{2'}$, $R^3$, X, Z, Y and q are as defined below.

The invention further relates to a pharmaceutical composition comprising a compound of formula I, and the use thereof.

DESCRIPTION OF THE INVENTION

The present invention relates to novel 1,2,4-triaminobenzene derivatives of formula I

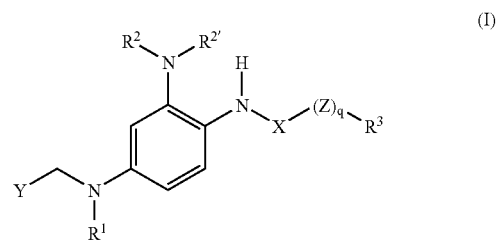

wherein
$R^1$ is selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, acyl, hydroxy-$C_{1-6}$-alk(en/yn)yl and hydroxy-$C_{3-8}$-cycloalk(en)yl;

$R^2$ and $R^{2'}$ are independently selected from the group consisting of hydrogen, $C_{1-6}$-alk(en/yn)yl, $C_{3-8}$-cycloalk(en) yl, aryl, $C_{3-8}$-cycloalk(en)yl-$C_{1-6}$-alk(en/yn)yl, aryl-$C_{1-6}$-alk (en/yn)yl, acyl, hydroxy-$C_{1-6}$-alk(en/yn)yl and hydroxy-$C_{3-8}$-cycloalk(en)yl;

$R^3$ is selected from the group consisting of hydrogen, $C_{1-6}$-alk(en/yn)yl, $C_{3-8}$-cycloalk(en)yl, aryl, $C_{3-8}$-cycloalk (en)yl-$C_{1-6}$-alk(en/yn)yl, aryl-$C_{1-6}$-alk(en/yn)yl, hydroxy-$C_{1-6}$-alk(en/yn)yl, aryl-$C_{3-8}$-cycloalk(en)yl, $NR^{10}R^{10'}$—$C_{1-6}$-alk(en/yn)yl, $NR^{10}R^{10'}$—$C_{3-8}$-cycloalk(en)yl and hydroxy-$C_{3-8}$-cycloalk(en)yl; wherein $R^{10}$ and $R^{10'}$ are independently selected from the group consisting of hydrogen, $C_{1-6}$-alk(en/yn)yl, $C_{3-8}$-cycloalk(en) yl, $C_{3-8}$-cycloalk(en)yl-$C_{1-6}$-alk(en/yn)yl, hydroxy-$C_{1-6}$-alk (en/yn)yl, hydroxy-$C_{3-8}$-cycloalk(en)yl, hydroxy-$C_{3-8}$-cycloalk(en)yl-$C_{1-6}$-alk(en/yn)yl, halo-$C_{1-6}$-alk(en/yn)yl, halo-$C_{3-8}$cycloalk(en)yl, halo-$C_{3-8}$-cycloalk(en)yl-$C_{1-6}$alk(en/yn)yl, cyano-$C_{1-6}$-alk(en/yn)yl, cyano-$C_{3-8}$-cycloalk(en)yl and cyano-$C_{3-8}$-cycloalk(en)yl-$C_{1-6}$-alk(en/yn)yl, or $R^{10}$ and $R^{10'}$ together with the nitrogen atom to which they are attached form a 4-8 membered saturated or unsaturated ring which optionally contains 1, 2 or 3 further heteroatoms;

X is CO or $SO_2$;

Z is O or $NR^4$, wherein $R^4$ is selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, hydroxy-$C_{1-6}$-alk(en/yn)yl and hydroxy-$C_{3-8}$-cycloalk(en)yl; or $R^3$ and $R^4$ together with the nitrogen atom to which they are attached form a 4-8 membered saturated or unsaturated ring which optionally contains 1, 2 or 3 further heteroatoms, the ring formed by $R^3$ and $R^4$ and the nitrogen atom is optionally substituted with one or more substituents independently selected from $C_{1-6}$-alk(en/yn)yl, aryl and aryl-$C_{1-6}$-alk(en/yn)yl;

q is 0 or 1;

and

Y represents a heteroaryl of formula II or III

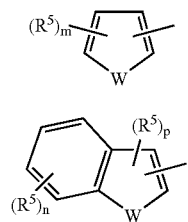

wherein

W is O or S;

m is 0, 1, 2 or 3;

n is 0, 1, 2, 3 or 4;

p is 0 or 1; and each $R^5$ is independently selected from the group consisting of $C_{1-6}$-alk(en/yn)yl, $C_{3-8}$-cycloalk(en)yl, aryl, $C_{3-8}$-cycloalk(en)yl-$C_{1-6}$-alk(en/yn)yl, aryl-$C_{1-6}$-alk(en/yn)yl, acyl, halogen, halo-$C_{1-6}$-alk(en/yn)yl, $C_{1-6}$-alk(en/yn)yloxy, —CO—$NR^6R^{6'}$, cyano, nitro, —$NR^7R^{7'}$, —S—$R^8$, —$SO_2R^8$ and $SO_2OR^8$;

wherein $R^6$ and $R^{6'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl and aryl;

$R^7$ and $R^{7'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, aryl and acyl; and $R^8$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, aryl and —$NR^9R^{9'}$; wherein $R^9$ and $R^{9'}$ are independently selected from the group consisting of hydrogen, $C_{1-6}$-alk(en/yn)yl, $C_{3-8}$cycloalk(en)yl and $C_{3-8}$-cycloalk(en)yl-$C_{1-6}$-alk(en/yn)yl;

or pharmaceutically acceptable salts thereof.

When q is 0 then $R^3$ is attached to X, whereas when q is 1 then $R^3$ is attached to Z, which is attached to X. X-$(Z)_q$-$R^3$ may thus represent X—$R^3$, X—O—$R^3$ or X—$NR^3R^4$.

In a particular embodiment, the present invention relates to a compound of formula I, wherein $R^1$, $R^2$, $R^{2'}$, X, and q are as defined above; and $R^3$ is selected from the group consisting of hydrogen, $C_{1-6}$-alk(en/yn)yl, $C_{3-8}$-cycloalk(en)yl, aryl, $C_{3-8}$-cycloalk(en)yl-$C_{1-6}$-alk(en/yn)yl, aryl-$C_{1-6}$-alk(en/yn)yl, hydroxy-$C_{1-6}$-alk(en/yn)yl and hydroxy-$C_{3-8}$-cycloalk(en)yl; and Z is as defined above with the proviso that $R^4$ is selected from the group consisting of hydrogen, $C_{1-6}$alk(en/yn)yl, $C_{3-8}$-cycloalk(en)yl, $C_{3-8}$-cycloalk(en)yl-$C_{1-6}$-alk(en/yn)yl, hydroxy-$C_{1-6}$-alk(en/yn)yl and hydroxy-$C_{3-8}$-cycloalk(en)yl; and Y is as defined above with the proviso that each $R^5$ is independently selected from the group consisting of $C_{1-6}$-alk(en/yn)yl, $C_{3-8}$-cycloalk(en)yl, aryl, $C_{3-8}$-cycloalk(en)yl-$C_{1-6}$-alk(en/yn)yl, aryl-$C_{1-6}$-alk(en/yn)yl, acyl, halogen, halo-$C_{1-6}$-alk(en/yn)yl, —CO—$NR^6R^{6'}$, cyano, nitro, —$NR^7R^{7'}$, —S—$R^8$, —$SO_2R^8$ and $SO_2OR^8$;

or pharmaceutically acceptable acid addition salts thereof.

In one embodiment, $R^1$ is selected from the group consisting of acyl, hydroxy-$C_{1-6}$-alk(en/yn)yl and hydroxy-$C_{3-8}$-cycloalk(en)yl.

In another embodiment, the invention relates to such compounds wherein $R^1$ is selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl.

In one preferred embodiment, the invention relates to such compounds wherein $R^1$ is selected from the group consisting of hydrogen and $C_{1-6}$-alk(en/yn)yl.

In a particular embodiment, the invention relates to such compounds wherein $R^1$ is a hydrogen atom.

In another particular embodiment, the invention relates to such compounds wherein $R^1$ is $C_{1-6}$-alk(en/yn)yl.

In one embodiment, at least one of $R^2$ and $R^{2'}$ is selected from the group consisting of aryl, aryl-$C_{1-6}$-alk(en/yn)yl, acyl, hydroxy-$C_{1-6}$-alk(en/yn)yl and hydroxy-$C_{3-8}$-cycloalk(en)yl.

In another embodiment, at least one of $R^2$ and $R^{2'}$ is selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl.

In yet another embodiment, the invention relates to such compounds wherein at least one of the substituents $R^2$ and $R^{2'}$ is a hydrogen atom.

In yet another embodiment, the invention relates to such compounds, wherein both $R^2$ and $R^{2'}$ are hydrogen atoms.

In one embodiment, $R^3$ is selected from the group consisting of hydroxy-$C_{1-6}$-alk(en/yn)yl, aryl-$C_{3-8}$-cycloalk(en)yl, $NR^{10}R^{10'}$—$C_{1-6}$-alk(en/yn)yl, $NR^{10}R^{10'}$—$C_{3-8}$-cycloalk(en)yl and hydroxy-$C_{3-8}$-cycloalk(en)yl; wherein $R^{10}$ and $R^{10'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano-$C_{1-6}$-alk(en/yn)yl, cyano-$C_{3-8}$-cycloalk(en)yl and cyano-$C_{3-8}$-cycloalk(en)yl-$C_{1-6}$-alk(en/yn)yl; or $R^{10}$ and $R^{10'}$ together with the nitrogen atom to which they are attached form a 4-8 membered saturated or unsaturated ring which optionally contains 1, 2 or 3 further heteroatoms.

In yet another embodiment, the invention relates to such compounds wherein q is 1, Z is $NR^4$, and $R^3$ is a hydrogen atom.

In yet another embodiment, the invention relates to such compounds wherein $R^3$ is different from a hydrogen atom.

In yet another embodiment, $R^3$ is selected from the group consisting of $C_{1-6}$-alk(en/yn)yl, $C_{3-8}$-cycloalk(en)yl, aryl, $C_{3-8}$-cycloalk(en)yl-$C_{1-6}$-alk(en/yn)yl and aryl-$C_{1-6}$-alk(en/yn)yl.

In yet another embodiment, the invention relates to such compounds wherein $R^3$ is selected from the group consisting of $C_{1-6}$-alk(en/yn)yl and aryl-$C_{1-6}$-alk(en/yn)yl.

In yet another embodiment, the invention relates to such compounds wherein $R^3$ is $C_{1-6}$-alk(en/yn)yl.

In yet another embodiment, $R^3$ is $C_{3-8}$-cycloalk(en)yl-$C_{1-6}$-alk(en/yn)yl.

In yet another embodiment, the invention relates to such compounds wherein $R^3$ is aryl-$C_{1-6}$-alk(en/yn)yl.

In one embodiment, the invention relates to such compounds wherein X is $SO_2$.

In yet another embodiment, the invention relates to such compounds wherein X is CO.

In one embodiment, q is 0.

In yet another embodiment, the invention relates to such compounds wherein X is CO and q is 0.

In yet another embodiment, the invention relates to such compounds wherein X is CO and q is 0 and $R^3$ is different from aryl.

In another embodiment, q is 1.

In one embodiment, the invention relates to such compounds wherein q is 1 and Z is $NR^4$.

In one embodiment, q is 1, Z is $NR^4$, and $R^3$ and $R^4$ together with the nitrogen atom to which they are attached form a 4-8 membered saturated or unsaturated ring which optionally contains 1, 2 or 3 further heteroatoms, the ring formed by $R^3$ and $R^4$ and the nitrogen atom is optionally substituted with one or more substituents independently selected from $C_{1-6}$-alk(en/yn)yl, aryl and aryl-$C_{1-6}$-alk(en/yn)yl.

In another embodiment, q is 1, Z is $NR^4$ and $R^4$ is selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, hydroxy-$C_{1-6}$-alk(en/yn)yl and hydroxy-$C_{3-8}$-cycloalk(en)yl.

In yet another embodiment, q is 1, Z is $NR^4$ and $R^4$ is a hydrogen atom.

In one embodiment, q is 1, Z is $NR^4$, and at least one of $R^3$ and $R^4$ is different from a hydrogen atom.

In yet another embodiment, the invention relates to such compounds wherein q is 1 and Z is an oxygen atom.

In yet another embodiment, the invention relates to such compounds wherein X is CO, q is 1 and Z is an oxygen atom.

In yet another embodiment, the invention relates to such compounds wherein $R^2$ and $R^{2'}$ are hydrogen atoms, X is CO, q is 1 and Z is an oxygen atom.

In yet another embodiment, the invention relates to such compounds wherein W is an oxygen atom.

In yet another embodiment, the invention relates to such compounds wherein W is a sulfur atom.

In yet another embodiment, the invention relates to such compounds wherein W is a sulphur atom and X is CO.

In yet another embodiment, the invention relates to such compounds wherein W is a sulphur atom and q is 0.

In yet another embodiment, the invention relates to such compounds wherein W is a sulphur atom, X is CO and q is 0.

In yet another embodiment, the invention relates to such compounds wherein W is a sulphur atom, q is 1 and Z is an oxygen atom.

In yet another embodiment, the invention relates to such compounds wherein W is a sulphur atom, X is CO, q is 1 and Z is an oxygen atom.

In yet another embodiment, m is 0.
In yet another embodiment, m is 1.
In yet another embodiment, m is 2.
In one embodiment, m is 3.
In yet another embodiment, n is 0.
In yet another embodiment, n is 1.
In one embodiment, n is 2, 3 or 4;
In one embodiment, p is 0.
In another embodiment, p is 1.

In one embodiment, at least one $R^5$ is selected from the group consisting of acyl, —CO—$NR^6R^{6'}$, nitro, —S—$R^8$ and $SO_2OR^8$.

In another embodiment, each $R^5$ is independently selected from the group consisting of $C_{1-6}$-alk(en/yn)yl, $C_{3-8}$-cycloalk(en)yl, aryl, $C_{3-8}$-cycloalk(en)yl-$C_{1-6}$-alk(en/yn)yl, aryl-$C_{1-6}$-alk(en/yn)yl, halogen, halo-$C_{1-6}$-alk(en/yn)yl, $C_{1-6}$-alk(en/yn)yloxy, cyano, —$NR^7R^{7'}$ and —$SO_2R^8$.

In yet another embodiment, each $R^5$ is independently selected from the group consisting of $C_{1-6}$-alk(en/yn)yl, aryl, halogen, $C_{1-6}$-alk(en/yn)yloxy, —$NR^7R^{7'}$ and —$SO_2R^8$.

In yet another embodiment, the invention relates to such compounds wherein each $R^5$ is independently selected from the group consisting of $C_{1-6}$-alk(en/yn)yl, halogen and —$SO_2R^8$ wherein $R^8$ is aryl.

In yet another embodiment, at least one substituent $R^5$ is $C_{1-6}$-alk(en/yn)yl.

In yet another embodiment, at least one substituent $R^5$ is aryl.

In yet another embodiment, at least one substituent $R^5$ is $C_{1-6}$-alk(en/yn)yloxy.

In yet another embodiment, at least one substituent $R^5$ is —$SO_2R^8$.

In yet another embodiment, at least one substituent $R^5$ is a halogen atom.

In yet another embodiment, at least one substituent $R^5$ is a halogen atom, which is selected from the group consisting of chloro, bromo and iodo.

In yet another embodiment, at least one substituent $R^5$ is fluoro.

In yet another embodiment, at least one substituent $R^5$ is chloro.

In yet another embodiment, at least one substituent $R^5$ is bromo.

In yet another embodiment, at least one substituent $R^5$ is —$NR^7R^{7'}$.

In one embodiment, at least one substituent $R^5$ is —$NR^7R^{7'}$; and at least one of $R^7$ and $R^{7'}$ is aryl or acyl.

In one embodiment, at least one substituent $R^5$ is —$NR^7R^{7'}$; and at least one of $R^7$ and $R^{7'}$ is selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl.

In another embodiment, at least one substituent $R^5$ is —$NR^7R^{7'}$; and at least one of $R^7$ and $R^{7'}$ is selected from the group consisting of hydrogen and $C_{1-6}$-alk(en/yn)yl.

In yet another embodiment, at least one substituent $R^5$ is —$NR^7R^{7'}$; and at least one of $R^7$ and $R^{7'}$ is $C_{1-6}$-alk(en/yn)yl.

In yet another embodiment, at least one substituent $R^5$ is —$NR^7R^{7'}$; and both $R^7$ and $R^{7'}$ are $C_{1-6}$-alk(en/yn)yl.

In one embodiment, at least one substituent $R^5$ is —$SO_2R^8$; and $R^8$ is —$NR^9R^{9'}$; wherein $R^9$ and $R^{9'}$ are independently selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl.

In one embodiment, at least one substituent $R^5$ is —$SO_2R^8$; and $R^8$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl and aryl.

In yet another embodiment, at least one substituent $R^5$ is —$SO_2R^8$; and $R^8$ is aryl.

In yet another embodiment, the invention relates to such compounds wherein Y is of formula II.

In yet another embodiment, the invention relates to such compounds wherein Y is of formula III.

In yet another embodiment, the invention relates to such compounds wherein Y is of formula IIb or IIIb

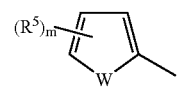
IIb

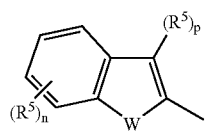
IIIb wherein W, m, n, p and $R^5$ are as defined above.

In yet another embodiment, the invention relates to such compounds wherein Y is of formula IIb.

In yet another embodiment, the invention relates to such compounds wherein m is 0 and Y is of formula IIb.

In yet another embodiment, the invention relates to such compounds wherein Y is of formula IIIb.

In yet another embodiment, the invention relates to such compounds wherein n is 0 and Y is of formula IIIb.

In yet another embodiment, the invention relates to such compounds wherein p is 0 and Y is of formula IIIb.

In yet another embodiment, the invention relates to such compounds wherein n is 0, p is 0 and Y is of formula IIIb.

In yet another embodiment, the invention relates to such compounds wherein Y is of formula IIIb and n+p is 1, in a particular aspect thereof n is 1 and p is 0 and in another particular aspect thereof n is 0 and p is 1.

In yet another embodiment, the invention relates to such compounds wherein Y is of formula IIIb and n+p is 2, in a particular aspect thereof n is 2 and p is 0; and in another particular aspect thereof n is 1 and p is 1.

In yet another embodiment, the invention relates to such compounds wherein Y is of the below formula $IIb^1$, $IIb^2$, $IIb^3$, $IIIb^1$, $IIIb^2$, $IIIb^3$ or $IIIb^4$:

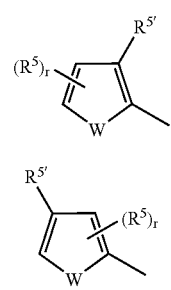
$IIb^1$ $IIb^2$

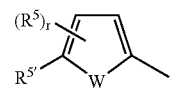
$IIb^3$

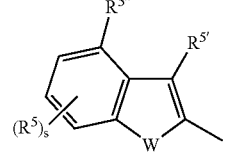
$IIIb^1$

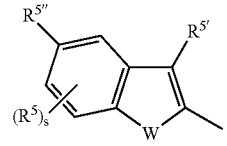
$IIIb^2$

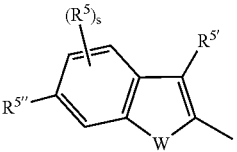
$IIIb^3$

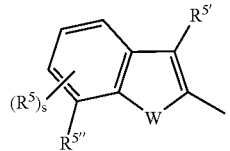
$IIIb^4$ wherein
W is as defined above;
r is 0, 1 or 2;
s is 0, 1, 2 or 3; and
$R^{5'}$ and $R^{5''}$ are independently defined as $R^5$ and each $R^5$ is independently as defined above.

In yet another embodiment, the invention relates to such compounds wherein:
m is 0 and Y is of formula IIb; or
n is 0 and Y is of formula IIIb; or
p is 0 and Y is of formula IIIb; or
n is 0, p is 0 and Y is of formula IIIb; or
Y is of formula IIIb and n+p is 1, in a particular aspect thereof n is 1 and p is 0 and in another particular aspect thereof n is 0 and p is 1; or
Y is of formula IIIb and n+p is 2, in a particular aspect thereof n is 2 and p is 0; and in another particular aspect thereof n is 1 and p is 1; or
Y is of the formula $IIIb^1$; or $IIb^2$; or $IIb^3$; or $IIIb^1$; or $IIIb^2$; or $IIIb^3$; or $IIIb^4$.

In yet another embodiment, the invention relates to such compounds wherein Y is of formula $IIb^1$; or $IIb^2$; or $IIb^3$; or wherein m is 0 and Y is of formula IIb.

In yet another embodiment, the invention relates to such compounds wherein Y is of formula $IIb^1$.

In yet another embodiment, the invention relates to such compounds wherein Y is of formula $IIb^2$.

In yet another embodiment, the invention relates to such compounds wherein Y is of formula $IIb^3$.

In yet another embodiment, the invention relates to such compounds wherein
Y is of formula $IIIb^1$; or $IIIb^2$; or $IIIb^3$; or $IIIb^4$; or n is 0 and Y is of formula IIIb; or
p is 0 and Y is of formula IIIb; or
n is 0, p is 0 and Y is of formula IIIb; or
Y is of formula IIIb and n+p is 1, in a particular aspect thereof n is 1 and p is 0 and in another particular aspect thereof n is 0 and p is 1; or
Y is of formula IIIb and n+p is 2, in a particular aspect thereof n is 2 and p is 0 and in another particular aspect thereof n is 1 and p is 1.

In yet another embodiment, the invention relates to such compounds wherein Y is of formula IIIb$^1$.

In yet another embodiment, the invention relates to such compounds wherein Y is of formula IIIb$^2$.

In yet another embodiment, the invention relates to such compounds wherein Y is of formula IIIb$^3$.

In yet another embodiment, the invention relates to such compounds wherein Y is of formula IIIb$^4$.

In yet another embodiment, the invention relates to such compounds wherein Y is of formula IIc or IIIc

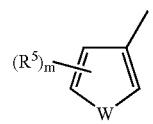

IIc

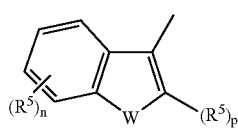

IIIc wherein W, m, n, p and R$^5$ are as defined above.

In yet another embodiment, the invention relates to such compounds wherein Y is of formula IIc.

In yet another embodiment, the invention relates to such compounds wherein m is 0 and Y is of formula IIc.

In yet another embodiment, the invention relates to such compounds wherein Y is of formula IIIc.

In yet another embodiment, the invention relates to such compounds wherein n is 0 and Y is of formula IIIc.

In yet another embodiment, the invention relates to such compounds wherein p is 0 and Y is of formula IIIc.

In yet another embodiment, the invention relates to such compounds wherein n is 0, p is 0 and Y is of formula IIIc.

In yet another embodiment, the invention relates to such compounds wherein Y is of formula IIIc and n+p is 1, in a particular aspect thereof n is 1 and p is 0 and in another particular aspect thereof n is 0 and p is 1.

In yet another embodiment, the invention relates to such compounds wherein Y is of formula IIIc and n+p is 2, in a particular aspect thereof n is 2 and p is 0 and in another particular aspect thereof n is 1 and p is 1.

In yet another embodiment, the invention relates to such compounds wherein Y is of the below formula IIc$^1$, IIc$^2$, IIc$^3$, IIIc$^1$, IIIc$^2$, IIIc$^3$ or IIIc$^4$:

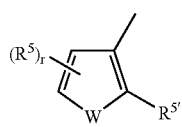

IIc$^1$

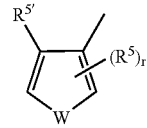

IIc$^2$

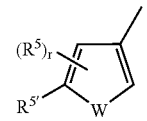

IIc$^3$

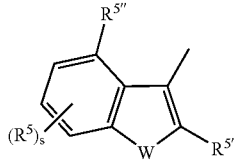

IIIc$^1$

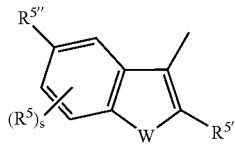

IIIc$^2$

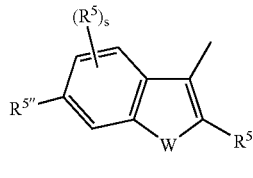

IIIc$^3$

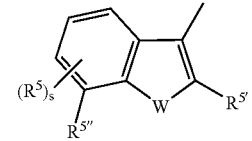

IIIc$^4$ wherein
W is as defined above;
r is 0, 1 or 2;
s is 0, 1, 2 or 3; and
R$^{5'}$ and R$^{5''}$ are independently defined as R$^5$ and each R$^5$ is independently as defined above.

In yet another embodiment, the invention relates to such compounds wherein:
m is 0 and Y is of formula IIc; or
n is 0 and Y is of formula IIIc; or
p is 0 and Y is of formula IIIc; or
n is 0, p is 0 and Y is of formula IIIc; or
Y is of formula IIIc and n+p is 1, in a particular aspect thereof n is 1 and p is 0 and in another particular aspect thereof n is 0 and p is 1; or
Y is of formula IIIc and n+p is 2, in a particular aspect thereof n is 2 and p is 0 and in another particular aspect thereof n is 1 and p is 1; or
Y is of the formula IIc$^1$; or IIc$^2$; or IIc$^3$; or IIIc$^1$; or IIIc$^2$; or IIIc$^3$; or IIIc$^4$.

In yet another embodiment, the invention relates to such compounds wherein Y is of formula IIc$^1$; or IIc$^2$; or IIc$^3$; or m is 0 and Y is of formula IIc.

In yet another embodiment, the invention relates to such compounds wherein Y is of formula IIc$^1$.

In yet another embodiment, the invention relates to such compounds wherein Y is of formula IIc$^2$.

In yet another embodiment, the invention relates to such compounds wherein Y is of formula IIc$^3$.

In yet another embodiment, the invention relates to such compounds wherein
Y is of formula IIIc$^1$; or IIIc$^2$; or IIIc$^3$; or IIIc$^4$; or
n is 0 and Y is of formula IIIc; or
p is 0 and Y is of formula IIIc; or
n is 0, p is 0 and Y is of formula IIIc; or
Y is of formula IIIc and n+p is 1, in a particular aspect thereof n is 1 and p is 0 and in another particular aspect thereof n is 0 and p is 1; or
Y is of formula IIIc and n+p is 2, in a particular aspect thereof n is 2 and p is 0 and in another particular aspect thereof n is 1 and p is 1.

In yet another embodiment, the invention relates to such compounds wherein Y is of formula IIIc$^1$.

In yet another embodiment, the invention relates to such compounds wherein Y is of formula IIIc$^2$.

In yet another embodiment, the invention relates to such compounds wherein Y is of formula IIIc$^3$.

In yet another embodiment, the invention relates to such compounds wherein Y is of formula IIIc$^4$.

In yet another embodiment, the invention relates to such compounds wherein r is 0.

In yet another embodiment, the invention relates to such compounds wherein r is 1.

In yet another embodiment, the invention relates to such compounds wherein r is 2.

In yet another embodiment, the invention relates to such compounds wherein s is 0

In yet another embodiment, the invention relates to such compounds wherein s is 1, 2 or 3.

In yet another embodiment, the invention relates to such compounds wherein Y of formula II represents
IIb$^1$; or IIb$^2$; or IIb$^3$; or IIc$^1$; or IIc$^2$; or IIc$^3$; or
a group of formula IIb wherein m is 0; or
a group of formula IIc wherein m is 0.

In yet another embodiment, the invention relates to such compounds wherein Y of formula II represents
IIb$^1$; or IIb$^2$; or IIb$^3$; or
a group of formula IIb wherein m is 0; or
a group of formula IIc wherein m is 0.

In yet another embodiment, the invention relates to such compounds wherein Y of formula III represents
IIIb$^1$; or IIIb$^2$; or IIIb$^3$; or IIIb$^4$; or IIIc$^1$; or IIIc$^2$; or IIIc$^3$; or IIIc$^4$; or
a group of formula IIIb wherein n is 0; or
a group of formula IIIb wherein p is 0; or
a group of formula IIIb wherein n is 0 and p is 0; or
a group of formula IIIb wherein n+p is 1, in a particular aspect thereof n is 1 and p is 0 and in another particular aspect thereof n is 0 and p is 1; or
Y is of formula IIIb and n+p is 2, in a particular aspect thereof n is 2 and p is 0 and in another particular aspect thereof n is 1 and p is 1;
a group of formula IIIc wherein n is 0; or
a group of formula IIIc wherein p is 0; or
a group of formula IIIc wherein n is 0 and p is 0; or
a group of formula IIIc wherein n+p is 1, in a particular aspect thereof n is 1 and p is 0 and in another particular aspect thereof n is 0 and p is 1; or
Y is of formula IIIc and n+p is 2, in a particular aspect thereof n is 2 and p is 0 and in another particular aspect thereof n is 1 and p is 1.

In yet another embodiment, the invention relates to such compounds wherein Y of formula III represents
IIIb$^2$; or IIIc$^2$; or
a group of formula IIIb wherein n is 0 and p is 0; or
a group of formula IIIc wherein n is 0 and p is 0.

In yet another embodiment, the invention relates to such compounds wherein m is 0 and Y is of formula II, in particular aspects thereof Y is of formula IIb or IIc.

In yet another embodiment m is 1, and Y is of formula II, in a particular aspect thereof Y is of formula IIb, and in more particular aspects thereof Y is of formula IIb$^1$, IIb$^2$ or IIb$^3$.

In yet another embodiment m is 1, R$^5$ is selected from the group consisting of C$_{1-6}$-alk(en/yn)yl and halogen, and Y is of formula II, in a particular aspect thereof Y is of formula IIb, and in more particular aspects thereof Y is of formula IIb$^1$, IIb$^2$ or IIb$^3$.

In yet another embodiment, the invention relates to such compounds wherein m is 1, R$^5$ is C$_{1-6}$alk(en/yn)yl and Y is of formula II, in a particular aspect thereof Y is of formula IIb, and in more particular aspects thereof Y is of formula IIb$^1$ or IIb$^3$.

In yet another embodiment, the invention relates to such compounds wherein m is 1, R$^5$ is a halogen atom such as bromo or chloro or fluoro, and Y is of formula II, in a particular aspect thereof Y is of formula IIb, and in more particular aspects thereof Y is of formula IIb$^1$, IIb$^2$ or IIb$^3$.

In yet another embodiment, the invention relates to such compounds wherein m is 1, R$^5$ is bromo or chloro, and Y is of formula II, in a particular aspect thereof Y is of formula IIb, and in more particular aspects thereof Y is of formula IIb$^1$, IIb$^2$ or IIb$^3$.

In yet another embodiment, the invention relates to such compounds wherein m is 1, R$^3$ is C$_{1-6}$-alk(en/yn)yl, and Y is of formula II, in a particular aspect thereof Y is of formula IIb, and in more particular aspects thereof Y is of formula IIb$^1$, IIb$^2$ or IIb$^3$, and in a most particular aspect thereof Y is of formula IIb$^3$.

In yet another embodiment, the invention relates to such compounds wherein R$^1$ is C$_{1-6}$-alk(en/yn)yl, m is 1, R$^5$ is C$_{1-6}$-alk(en/yn)yl or halogen and Y is of formula II, in a particular aspect thereof Y is of formula IIb, and in a more particular aspect thereof Y is of formula IIb$^3$.

In yet another embodiment, the invention relates to such compounds wherein n is 0, p is 0 and Y is of formula III; in particular aspects thereof Y is of formula IIIb or IIIc.

In yet another embodiment, the invention relates to such compounds wherein n is 1 and Y is of formula III, in particular aspects thereof Y is of formula IIIb or IIIc, and in more particular aspects thereof Y is of formula IIIb$^2$, IIIb$^3$ or IIIc$^2$.

In yet another embodiment, the invention relates to such compounds wherein n+p is 1 and Y is of formula III; in a particular aspect thereof Y is of formula IIIc; and in a more particular aspect thereof Y is of formula IIIc$^2$.

In yet another embodiment, the invention relates to such compounds wherein n+p is 2 and Y is of formula III; in a particular aspect thereof Y is of formula IIIb; and in a more particular aspect thereof Y is of formula IIIb$^2$ or IIIb$^3$.

In yet another embodiment, Y is not of formula II when W is an oxygen atom.

In yet another embodiment, the compound of formula I contains no more than 3 aryl groups as defined herein.

The compounds of the following list and pharmaceutically acceptable salts thereof are preferred:
{2-Amino-4-[(5-chloro-thiophen-2-ylmethyl)-methyl-amino]-phenyl}-carbamic acid ethyl ester;

{2-Amino-4-[(5-chloro-thiophen-2-ylmethyl)-amino]-phenyl}-carbamic acid ethyl ester;
{2-Amino-4-[(5-methyl-thiophen-2-ylmethyl)-methyl-amino]-phenyl}-carbamic acid ethyl ester;
{2-Amino-4-[(5-bromo-thiophen-2-ylmethyl)-amino]-phenyl}-carbamic acid ethyl ester;
{2-Amino-4-[(6-chloro-3-methoxy-benzo[b]thiophen-2-ylmethyl)-amino]-phenyl}-carbamic acid ethyl ester;
{2-Amino-4-[(benzo[b]thiophen-2-ylmethyl)-amino]-phenyl}-carbamic acid ethyl ester;
{2-Amino-4-[(5-methyl-thiophen-2-ylmethyl)-amino]-phenyl}-carbamic acid ethyl ester;
{2-Amino-4-[(4-bromo-3-methoxy-thiophen-2-ylmethyl)-amino]-phenyl}-carbamic acid ethyl ester;
{2-Amino-4-[(5-phenyl-thiophen-2-ylmethyl)-amino]-phenyl}-carbamic acid ethyl ester;
{2-Amino-4-[(3-chloro-thiophen-2-ylmethyl)-amino]-phenyl}-carbamic acid ethyl ester;
(2-Amino-4-{[4-(4-chloro-benzenesulfonyl)-3-methyl-thiophen-2-ylmethyl]-amino}-phenyl)-carbamic acid ethyl ester;
{2-Amino-4-[(3-methyl-thiophen-2-ylmethyl)-amino]-phenyl}-carbamic acid ethyl ester;
{2-Amino-4-[(5-fluoro-benzofuran-3-ylmethyl)-amino]-phenyl}-carbamic acid ethyl ester;
{2-Amino-4-[(thiophen-2-ylmethyl)-amino]-phenyl}-carbamic acid ethyl ester;
{2-Amino-4-[(4-bromo-thiophen-2-ylmethyl)-amino]-phenyl}-carbamic acid ethyl ester;
{2-Amino-4-[(5-ethyl-thiophen-2-ylmethyl)-amino]-phenyl}-carbamic acid ethyl ester;
{2-Amino-4-[(thiophen-3-ylmethyl)-amino]-phenyl}-carbamic acid ethyl ester;
{2-Amino-4-[(5-chloro-thiophen-2-ylmethyl)-ethyl-amino]-phenyl}-carbamic acid ethyl ester;
{2-Amino-4-[(benzo[b]thiophen-3-ylmethyl)-amino]-phenyl}-carbamic acid ethyl ester;
{2-Amino-4-[(5-dimethyl-amino-benzo[b]thiophen-3-ylmethyl)-amino]-phenyl}-carbamic acid ethyl ester;
{2-Amino-4-[(5-dimethyl-amino-3-methyl-benzo[b]thiophen-2-ylmethyl)-amino]-phenyl}-carbamic acid ethyl ester;
{2-Amino-4-[(5-fluoro-thiophen-2-ylmethyl)-amino]-phenyl}-carbamic acid ethyl ester;
{2-Amino-4-[(benzo[b]thiophen-2-ylmethyl)-amino]-phenyl}-carbamic acid propyl ester;
{2-Amino-4-[(benzo[b]thiophen-3-ylmethyl)-amino]-phenyl}-carbamic acid propyl ester;
N-{2-Amino-4-[(5-chloro-thiophen-2-ylmethyl)amino]-phenyl}-2-(4-fluoro-phenyl)-acetamide; and
N-{2-Amino-4-[(5-chloro-thiophen-2-ylmethyl)amino]-phenyl}-3,3-dimethyl-butyramide.

In a particular aspect, the compounds of the following list and pharmaceutically acceptable acid addition salts thereof are preferred:
{2-Amino-4-[(5-chloro-thiophen-2-ylmethyl)-methyl-amino]-phenyl}-carbamic acid ethyl ester;
{2-Amino-4-[(5-chloro-thiophen-2-ylmethyl)-amino]-phenyl}-carbamic acid ethyl ester;
{2-Amino-4-[(5-methyl-thiophen-2-ylmethyl)-methyl-amino]-phenyl}-carbamic acid ethyl ester;
{2-Amino-4-[(5-bromo-thiophen-2-ylmethyl)-amino]-phenyl}-carbamic acid ethyl ester;
{2-Amino-4-[(6-chloro-3-methoxy-benzo[b]thiophen-2-ylmethyl)-amino]-phenyl}-carbamic acid ethyl ester;
{2-Amino-4-[(benzo[b]thiophen-2-ylmethyl)-amino]-phenyl}-carbamic acid ethyl ester;
{2-Amino-4-[(5-methyl-thiophen-2-ylmethyl)-amino]-phenyl}-carbamic acid ethyl ester;
{2-Amino-4-[(4-bromo-3-methoxy-thiophen-2-ylmethyl)-amino]-phenyl}-carbamic acid ethyl ester;
{2-Amino-4-[(5-phenyl-thiophen-2-ylmethyl)-amino]-phenyl}-carbamic acid ethyl ester;
{2-Amino-4-[(3-chloro-thiophen-2-ylmethyl)-amino]-phenyl}-carbamic acid ethyl ester;
(2-Amino-4-{[4-(4-chloro-benzenesulfonyl)-3-methyl-thiophen-2-ylmethyl]-amino}-phenyl)-carbamic acid ethyl ester;
{2-Amino-4-[(3-methyl-thiophen-2-ylmethyl)-amino]-phenyl}-carbamic acid ethyl ester;
{2-Amino-4-[(5-fluoro-benzofuran-3-ylmethyl)-amino]-phenyl}-carbamic acid ethyl ester;
{2-Amino-4-[(thiophen-2-ylmethyl)-amino]-phenyl}-carbamic acid ethyl ester;
{2-Amino-4-[(4-bromo-thiophen-2-ylmethyl)-amino]-phenyl}-carbamic acid ethyl ester;
{2-Amino-4-[(5-ethyl-thiophen-2-ylmethyl)-amino]-phenyl}-carbamic acid ethyl ester;
{2-Amino-4-[(thiophen-3-ylmethyl)-amino]-phenyl}-carbamic acid ethyl ester; and
{2-Amino-4-[(5-chloro-thiophen-2-ylmethyl)-ethyl-amino]-phenyl}-carbamic acid ethyl ester.

In one aspect, the invention provides a pharmaceutical composition comprising at least one compound of formula I as defined above or a pharmaceutically acceptable salt thereof in a therapeutically effective amount together with one or more pharmaceutically acceptable carriers or diluents.

In one particular aspect, the invention provides a pharmaceutical composition comprising at least one compound of formula I as defined above or a pharmaceutically acceptable acid addition salt thereof in a therapeutically effective amount together with one or more pharmaceutically acceptable carriers or diluents.

The invention provides a pharmaceutical composition for oral or parenteral administration, said pharmaceutical composition comprising at least one compound of formula I or a salt thereof in a therapeutically effective amount together with one or more pharmaceutically acceptable carriers or diluents.

In one embodiment, the compounds of the invention may be administered as the only therapeutically effective compound.

In another embodiment, the compounds of the invention may be administered as a part of a combination therapy, i.e. the compounds of the invention may be administered in combination with other therapeutically effective compounds having e.g. anti-convulsive properties. The effects of such other compounds having anti-convulsive properties may include, but not be limited to, activities on:
  ion channels such as sodium, potassium or calcium channels
  the excitatory amino acid systems e.g. blockade or modulation of NMDA receptors
  the inhibitory neurotransmitter systems e.g. enhancement of GABA release or blockade of GABA-uptake and/or membrane stabilisation effects.

Current anti-convulsive medications include, but are not limited to, tiagabine, carbamazepine, sodium valproate, lamotrigine, gabapentin, pregabalin, ethosuximide, levetiracetam, phenytoin, topiramate, zonisamide as well as members of the benzodiazepine and barbiturate class.

The compounds of the invention are considered useful for increasing ion flow in a voltage-dependent potassium channel.

The compounds of the invention are considered useful for preventing, treating and/or inhibiting a disorder or condition being responsive to an increased ion flow in a potassium channel such as the KCNQ family potassium ion channels.

In one aspect, the compounds of the invention have been found to have effect on potassium channels of the KCNQ family, in particular on the KCNQ2 subunit.

According to one aspect, the compounds of the invention are considered to be useful for preventing, treating and/or inhibiting a variety of disorders of the central nervous system such as seizure disorders such as convulsions, epilepsy and status epilepticus; anxiety disorders such as anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia and specific phobias.

Accordingly, the compounds of the invention are considered to be useful for preventing, treating and/or inhibiting a variety of disorders of the central nervous system such as:

seizure disorders such as convulsions, epilepsy and status epilepticus;

neuropathic pain such as allodynia, hyperalgesic pain, phantom pain, neuropathic pain related to diabetic neuropathy and neuropathic pain related to migraine;

anxiety disorders such as anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia, specific phobias;

neurodegenerative disorders such as Alzheimer's disease, Huntington's chorea, multiple sclerosis, amyotrophic lateral sclerosis, AIDS-induced encephalopathy and other infection-related encephalopathies being caused by rubella viruses, herpes viruses, borrelia and by unknown pathogens, Creutzfeld-Jakob disease, Parkinson's disease, trauma-induced neurodegenerations, and neuronal hyperexcitation states such as in medicament withdrawal or by intoxication, neurodegenerative disorders of the peripheral nervous system such as polyneuropathies and polyneuritides.

Accordingly, the compounds of the invention are considered useful for preventing, treating and/or inhibiting disorders or conditions such as seizure disorders, neuropathic and migraine pain disorders, anxiety disorders and neurodegenerative disorders.

According to one particular aspect, the compounds of the invention are considered to be useful for preventing, treating and/or inhibiting seizure disorders such as convulsions, epilepsy and status epilepticus.

According to another particular aspect, the compounds of the invention are considered useful for preventing, treating and/or inhibiting neuropathic and migraine pain disorders such as allodynia, hyperalgesic pain, phantom pain, neuropathic pain related to diabetic neuropathy and neuropathic pain related to migraine.

The compounds of the invention are further considered useful for preventing, treating and/or inhibiting anxiety disorders such as anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia, anxiety disorder due to general medical condition and substance-induced anxiety disorder and specific phobias.

The compounds of the invention are further considered useful for preventing, treating and/or inhibiting neurodegenerative disorders such as Alzheimer's disease, Huntington's chorea, multiple sclerosis, amyotrophic lateral sclerosis, AIDS-induced encephalopathy and other infection-related encephalopathies being caused by rubella viruses, herpes viruses, borrelia and by unknown pathogens, Creutzfeld-Jakob disease, Parkinson's disease, trauma-induced neurodegenerations, and neuronal hyperexcitation states such as in medicament withdrawal or by intoxication.

In another aspect, the invention provides compounds showing effect in one or more of the following tests:

"Relative efflux through the KCNQ2 channel"
  Which is a measure of the potency of the compound at the target channel "Maximum electroshock"
  Which is a measure of seizures induced by non-specific CNS stimulation by electrical means "Pilocarpine induced seizures"
  Seizures induced by pilocarpine are often difficult to treat with many existing antiseizure medications and so reflect a model of "drug resistant seizures"

"Electrical seizure-threshold tests" and "Chemical seizure-threshold tests"
  These models measure the threshold at which seizures are initiated, thus being models that detect whether compounds could delay seizure initiation.

"Amygdala kindling"
  Which is used as a measure of disease progression, as in normal animals the seizures in this model get more severe as the animal receives further stimulations.

According to one particular aspect of the invention, the compounds are KCNQ2 active with an $EC_{50}$ of less than 15000 nM as measured by the test "Relative efflux through the KCNQ2 channel" which is described below.

According to one particular aspect of the invention, the compounds are KCNQ2 active with an $EC_{50}$ of less than 1500 nM as measured by the test "Relative efflux through the KCNQ2 channel" which is described below.

According to another particular aspect of the invention, the compounds are KCNQ2 active with an $EC_{50}$ of less than 150 nM as measured by the test "Relative efflux through the KCNQ2 channel" which is described below.

According to another particular aspect of the invention, the compounds have an $ED_{50}$ of less than 15 mg/kg in the test "Maximum electroshock" which is described below.

According to yet another particular aspect of the invention, the compounds have an $ED_{50}$ of less than 5 mg/kg in the test "Maximum electroshock" which is described below.

According to one particular aspect of the invention, the compounds have an $ED_{50}$ of less than 5 mg/kg in the "Electrical seizure—threshold test" and/or "Chemical seizure—threshold test" which is described below.

Some compounds have few or clinically insignificant side effects. Some of the compounds are thus tested in models of the unwanted sedative, hypothermic and ataxic actions of the compounds.

Some compounds have an appropriate half-life and an appropriate clearance meaning that patients only have to take their tablets e.g. once or twice daily. This is easy for the patient to remember and so aids compliance with the drug therapy.

Some of the compounds have a large therapeutic index between anticonvulsant efficacy and side-effects such as impairment of locomotor activity or ataxic effects as measured by performance on a rotating rod. This means that the compounds will expectedly be well tolerated in patients permitting high doses to be used before side-effects are seen. Thereby compliance with the therapy will expectedly be good and administration of high doses may be permitted making the treatment more efficacious in patients who would otherwise have side effects with other medications.

Definitions

The term heteroatom refers to a nitrogen, oxygen or sulphur atom.

Halogen means fluoro, chloro, bromo or iodo.

The expression $C_{1-6}$-alk(en/yn)yl means a $C_{1-6}$-alkyl, $C_{2-6}$-alkenyl or a $C_{2-6}$-alkynyl group.

The term $C_{1-6}$-alkyl refers to a branched or unbranched alkyl group having from one to six carbon atoms inclusive, including but not limited to methyl, ethyl, 1-propyl, 2-propyl, 1-butyl, 2-butyl, 2-methyl-2-propyl, 2-2-dimethyl-1-propyl and 2-methyl-1-propyl.

Similarly, $C_{2-6}$-alkenyl and $C_{2-6}$-alknyl, respectively, designate such groups having from two to six carbon atoms, including one double bond and one triple bond respectively, including but not limited to ethenyl, propenyl, butenyl, ethynyl, propynyl and butynyl.

The expression $C_{3-8}$-cycloalk(en)yl means a $C_{3-8}$-cycloalkyl- or cycloalkenyl group.

The term $C_{3-8}$-cycloalkyl designates a monocyclic or bicyclic carbocycle having three to eight C-atoms, including, but not limited to, cyclopropyl, cyclopentyl, cyclohexyl, etc.

The term $C_{3-8}$-cycloalkenyl designates a monocyclic or bicyclic carbocycle having three to eight C-atoms and including one double bond.

When two substituents together with the nitrogen atom to which they are attached form a 4-8 membered saturated or unsaturated ring which optionally contains 1, 2 or 3 furter heteroatoms, then a monocyclic ring system is formed by 4 to 8 atoms selected from the nitrogen atom, 1-7 carbon atoms and 0-3 heteroatoms selected from N, S or O. Examples of such ring systems are azetidine, beta-lactame, pyrrolidine, piperidine, piperazine, morpholine, pyrrole, oxazolidine, thiazolidine, imidazolidine, tetrazole and pyrazole.

The term aryl refers to aromatic systems such as pyridine, thiazole, oxazole, phenyl, naphtyl, thiophene and furan, which are optionally substituted with one or more substituents independently being hydroxy, halogen, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, $C_{1-6}$-alkoxy, $C_{3-8}$-alkoxy, acyl, nitro or cyano, —CO—NH—$C_{1-6}$-alk(en/yn)yl, —CO—N($C_{1-6}$-alk(en/yn)yl)$_2$, —NH—$C_{1-6}$-alk(en/yn)yl, —N($C_{1-6}$-alk(en/yn)yl)$_2$, —S—$C_{1-6}$-alk(en/yn)yl, —SO$_2$—$C_{1-6}$-alk(en/yn)yl, —SO$_2$O—$C_{1-6}$-alk(en/yn)yl, —NH$_2$, —SO$_2$N($C_{1-6}$-alk(en/yn)yl)$_2$ or —SO$_2$NH—$C_{1-6}$-alk(en/yn)yl; or two adjacent substituents may together with the aromatic group to which they are attached form a 4-8 membered ring, which optionally contains one or two heteroatoms.

When two adjacent substituents together with the aromatic group to which they are attached form a 4-8 membered ring, which optionally contains one or two heteroatoms, then a ring system is formed by 4-8 atoms selected from 3-8 carbonatoms and 0-2 heteroatoms selected from N, S, or O. Such two adjacent substituents may together form:

—(CH$_2$)$_{n''}$—CH$_2$—, CH=CH—(CH$_2$)$_{m''}$—, —CH$_2$—CH=CH—(CH$_2$)$_{p''}$—, —CH=CH—CH=CH—, —(CH$_2$)$_{n''}$—O—, —O—(CH$_2$)$_{m''}$—O—, —CH$_2$—O—(CH$_2$)$_{p''}$—O—, —CH$_2$—O—CH$_2$—O—CH$_2$—, —(CH$_2$)$_{n''}$—S—, —S—(CH$_2$)$_{m''}$—S—, —CH$_2$—S—(CH$_2$)$_{p''}$—S—, —CH$_2$—S—CH$_2$—S—CH$_2$—, —(CH$_2$)$_{n''}$—NH—, —NH—(CH$_2$)$_{m''}$—NH—, —CH$_2$—NH—(CH$_2$)$_{p''}$—NH—, —CH=CH—NH—, —O—(CH$_2$)$_{m''}$—NH—, —CH$_2$—O—(CH$_2$)$_{p''}$—NH— or —O—(CH$_2$)$_{m''}$—NH—CH$_2$—, (CH$_2$)$_{p''}$—NH—CH$_2$—, —S—(CH$_2$)$_{m''}$—NH—, —N=CH—NH—, —N=CH—O— or —N=CH—S—, wherein m" is 1, 2 or 3, n" is 2, 3 or 4 and p" is 1 or 2.

As used herein, the term acyl refers to formyl, $C_{1-6}$-alk(en/yn)ylcarbonyl, $C_{3-8}$-cycloalk(en)ylcarbonyl, arylcarbonyl, aryl-$C_{1-6}$-alk(en/yn)ylcarbonyl or a $C_{3-8}$-cycloalk(en)yl-$C_{1-6}$-alk(en/yn)yl-carbonyl group, wherein $C_{1-6}$-alk(en/yn)yl, $C_{3-8}$-cycloalk(en)yl and aryl are as defined above.

The term halo-$C_{1-6}$-alk(en/yn)yl designates $C_{1-6}$-alk(en/yn)yl being substituted with one or more halogen atoms, including but not limited to trifluormethyl. Similarly, halo-$C_{3-8}$-cycloalk(en)yl designates $C_{3-8}$-cycloalk(en)yl being substituted with one or more halogen atoms and halo-$C_{3-8}$-cycloalk(en)yl-$C_{1-6}$alk(en/yn)yl, designates $C_{3-8}$-cycloalk(en)yl-$C_{1-6}$alk(en/yn)yl being substituted with one or more halogen atoms.

In the term $C_{3-8}$-cycloalk(en)yl-$C_{1-6}$-alk(en/yn)yl, $C_{3-8}$-cycloalk(en)yl and $C_{1-6}$-alk(en/yn)yl are as defined above.

Furthermore, terms such as hydroxy-$C_{1-6}$-alk(en/yn)yl, hydroxy-$C_{3-8}$-cycloalk(en)yl, aryl-$C_{1-6}$-alk(en/yn)yl, $C_{1-6}$alk(en/yn)yloxy, $C_{3-8}$-cycloalk(en)yloxy, $C_{1-6}$-alk(en/yn)ylcarbonyl, $C_{3-8}$-cycloalk(en)ylcarbonyl, arylcarbonyl, aryl-$C_{1-6}$-alk(en/yn)ylcarbonyl, $C_{3-8}$-cycloalk(en)yl-$C_{1-6}$-alk(en/yn)ylcarbonyl, aryl-$C_{3-8}$-cycloalk(en)yl, hydroxy-$C_{3-8}$-cycloalk(en)yl-$C_{1-6}$-alk(en/yn)yl, hydroxy-$C_{1-6}$-alk(en/yn)yl-$C_{3-8}$-cycloalk(en)yl, cyano-$C_{1-6}$-alk(en/yn)yl, cyano-$C_{3-8}$-cycloalk(en)yl, cyano-$C_{3-8}$-cycloalk(en)yl-$C_{1-6}$-alk(en/yn)yl, $NR^{10}R^{10'}$—$C_{1-6}$-alk(en/yn)yl and $NR^{10}R^{10'}$—$C_{3-8}$-cycloalk(en)yl etc. designate groups in which the $C_{1-6}$-alk(en/yn)yl, $C_{3-8}$-cycloalk(en)yl and aryl are as defined above.

The salts of the invention are preferably pharmaceutically acceptable salts. Such salts include pharmaceutically acceptable acid addition salts, pharmaceutically acceptable metal salts, ammonium and alkylated ammonium salts.

The pharmaceutically acceptable salts of the invention are preferably acid addition salts.

Acid addition salts include salts of inorganic acids as well as organic acids.

The acid addition salts of the invention are preferably pharmaceutically acceptable salts of the compounds of the invention formed with non-toxic acids.

Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic and theophylline acetic acids, as well as the 8-halotheophyllines, for example 8-bromotheophylline.

Exemplary of such inorganic salts are those with hydrochloric, hydrobromic, sulfuric, sulfamic, phosphoric and nitric acids. Such acid addition salts can be formed by methods known to the person skilled in the art. Further examples of pharmaceutically acceptable inorganic or organic acid addition salts include the pharmaceutically acceptable salts listed in *J. Pharm. Sci.* 1977, 66, 2, which is incorporated herein by reference.

Also intended as pharmaceutically acceptable acid addition salts are the hydrates, which the present compounds are able to form.

Furthermore, when a double bond or a fully or partially saturated ring system is present in the molecule, geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention. Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention contain chiral centres and such compounds exist in the form of isomers (i.e. enantiomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization of d- or l-tartrates, mandelates or camphorsulphonate salts. The compounds of the present invention may also be resolved by the formation of diastereomeric derivatives.

Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981).

Optically active compounds can also be prepared from optically active starting materials.

The invention also encompasses prodrugs of the present compounds, which on administration undergo chemical conversion by metabolic processes before becoming pharmacologically active substances. In general, such prodrugs will be functional derivatives of the compounds of the general formula I, which are readily convertible in vivo into the required compound of the formula I. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

Whenever mentioned in relation to the compounds of the formulas I, the terms epilepsy and epilepsies embrace any of the epilepsies, epileptic syndromes and epileptic seizures referred to in International League Against Epilepsy: Proposal for revised clinical and electroencephalographic classification of epileptic seizures. Commission on Classification and Terrninology of the International League Against Epilepsy. *Epilepsia* 1981 22: 489-501 and in International League Against Epilepsy: Proposal for revised classification of epilepsies and epileptic syndromes. Conmmission on Classification and Terminology of the International League Against Epilepsy. *Epilepsia* 1989 30(4): 389-399.

Pharmaceutical Compositions

The compounds of this invention are generally utilized as the free base or as a pharmaceutically acceptable salt thereof. Representative examples are mentioned above.

If desired, the pharmaceutical composition of the invention may comprise the compound of formula I in combination with further pharmacologically active substances such as those described in the foregoing.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

The pharmaceutical compositions of this invention or those which are manufactured in accordance with this invention may be administered by any suitable route, for example orally in the form of tablets, capsules, powders, granules, pellets, a troche dragees, pills or lozenges, solutions or suspensions in aqueous or non-aqueous liquids, or oil-in-water or water-in-oil liquid emulsions, elixirs, syrups, etc., or parenterally in the form of solutions for injection. Other pharmaceutical compositions for parenteral administration include dispersions, suspensions or emulsions as well as sterile powders to be reconstituted in sterile injectable solutions or dispersions prior to use. Depot injectable formulations are also contemplated as being within the scope of the present invention. Other suitable administration forms include suppositories, sprays, ointments, cremes, gels, inhalants, dermal patches, implants etc.

For preparing such compositions, methods well known in the art may be used, and any pharmaceutically acceptable carriers, diluents, excipients or other additives normally used in the art may be used.

Conveniently, the compounds of the invention are administered in unit dosage form containing said compounds in an amount of about 0.01 to 100 mg. The total daily dose is usually in the range of about 0.05-500 mg or even 0.05-1500 mg or 0.05-3000 mg, and most preferably about 0.1 to 50 mg of the active compound of the invention. For parenteral routes such as intravenous, intrathecal, intramuscular and similar administration, typically, doses are in the order of about half the dose employed for oral administration.

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995. The formulations may conveniently be presented in unit dosage form by methods known in the art of pharmacy.

Any other adjuvants or additives usually used for such purposes such as colourings, flavourings, preservatives etc. may be used provided that they are compatible with the active ingredients.

The pharmaceutical formulations of the invention may be prepared by conventional methods in the art. Tablets may e.g. be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Where appropriate, a solid dosage form may be prepared with coatings such as enteric coatings or they can be formulated so as to provide controlled release of the active ingredient such as sustained or prolonged release according to methods well known in the art.

If a liquid carrier is used, the preparation may be in the form of a syrup, emulsion, soft gelatine capsule or sterile injectable liquid such as an aqueous or non-aqueous liquid suspension or solution.

For parenteral administration, solutions of the novel compounds of the invention in sterile aqueous solution, aqueous propylene glycol, aqueous vitamin E or sesame or peanut oil may be employed. Solutions for injections may be prepared by dissolving the active ingredient and possible additives in a part of the solvent for injection, preferably sterile water, adjusting the solution to desired volume, sterilising the solution and filling it in suitable ampules or vials. Any suitable additive conventionally used in the art may be added, such as tonicity agents, preservatives, antioxidants, etc. Accordingly, such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of liquid carriers are syrup, peanut oil, olive oil, phospho lipids, fatty acids, fatty acid amines, polyoxyethylene and water. Similarly, the carrier or diluent may include any sustained release material known in the art, such as glyceryl monostearate or glyceryl distearate, alone or mixed with a wax.

Typical examples of recipes for the formulation of the invention are as follows:

| 1) Tablets containing 5.0 mg of a compound of the invention calculated as the free base: | |
| --- | --- |
| Compound of formula I | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |
| 2) Tablets containing 0.5 mg of a compound of the invention calculated as the free base: | |
| Compound of formula I | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |
| 3) Syrup containing per milliliter: | |
| Compound of formula I | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 mL |
| Flavour | 0.05 mg |
| Saccharin sodium | 0.5 mg |
| Water | ad 1 mL |
| 4) Solution for injection containing per milliliter: | |
| Compound of formula I | 0.5 mg |
| Sorbitol | 5.1 mg |
| Acetic Acid | 0.05 mg |
| Saccharin sodium | 0.5 mg |
| Water | ad 1 mL |

Preparation of the Compounds of the Invention

The compounds of the invention of the general formula I, wherein $R^1$, $R^2$, $R^{2'}$, $R^3$, X, Y, Z and q are as defined above are prepared by the methods as represented in the scheme and as described below:

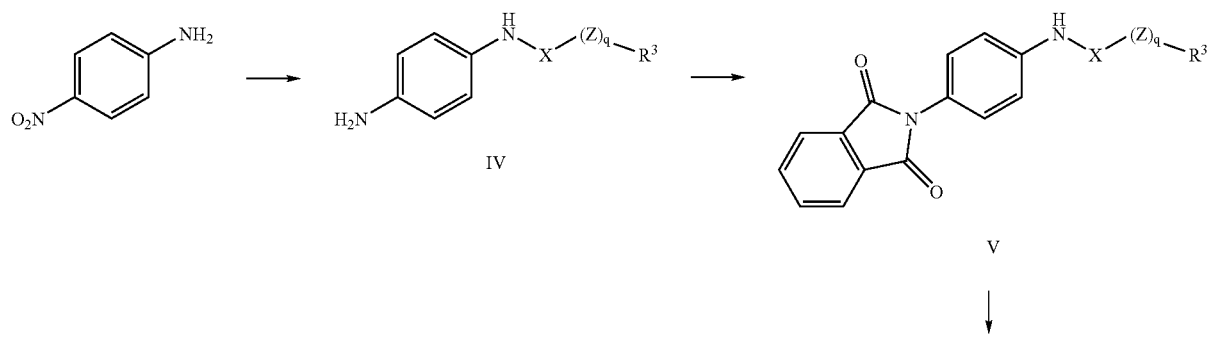

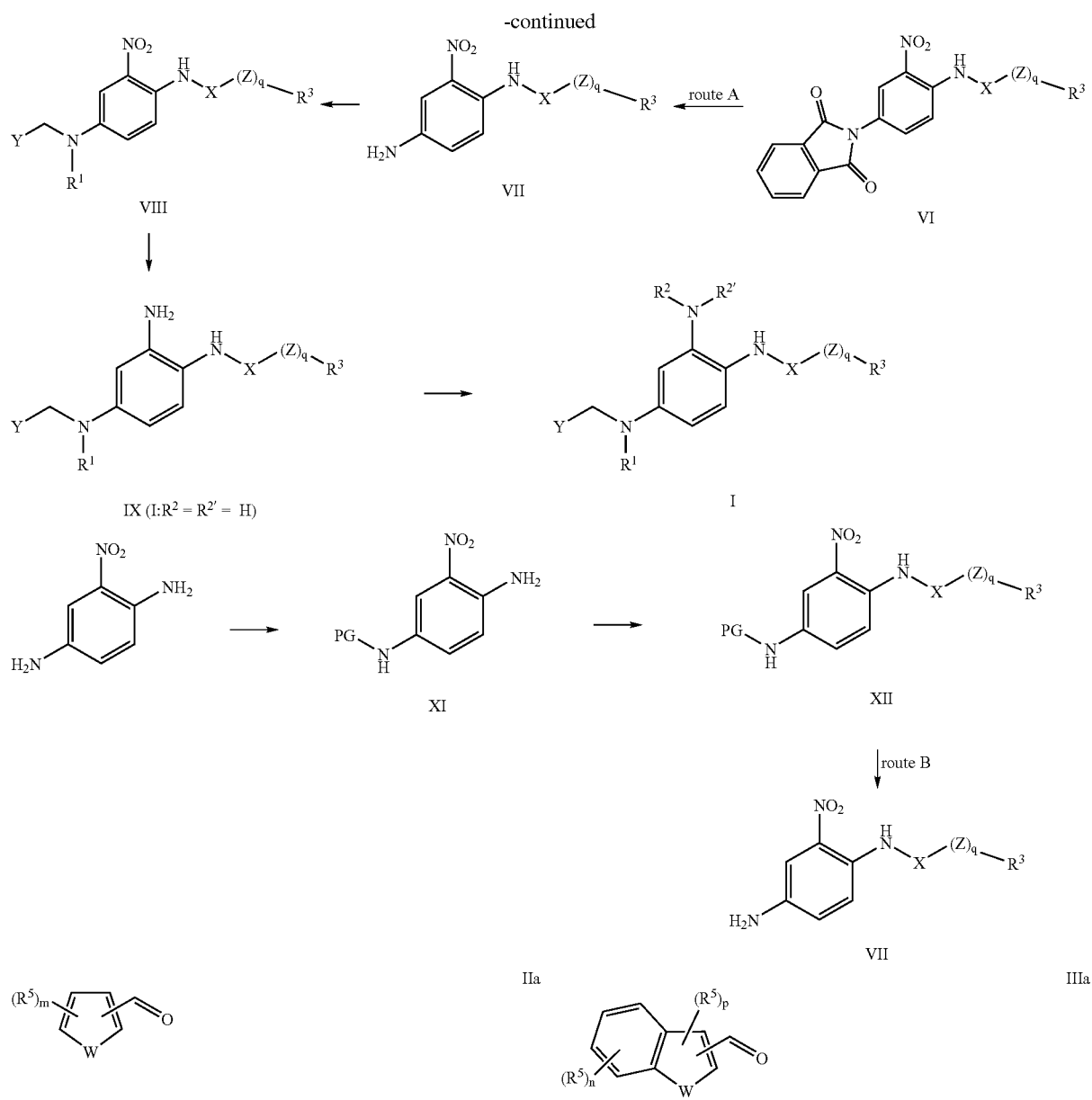

In the below, any of $R^1$, $R^2$, $R^{2'}$, $R^3$, $R^4$, $R^5$, $R^6$, $R^{6'}$, $R^7$, $R^{7'}$, $R^8$, $R^9$, $R^{9'}$, $R^{10}$, $R^{10'}$, X, Y, Z, W, m, n, p and q are as defined above.

Compounds of the general formula VII are prepared according to methods known to chemists skilled in the art (v. Bebenburg et al. *Chemiker Zeitung* 1979, Sonderdruck 103, 3-15) and as outlined below:

Compounds of the general formula IV are prepared by the reaction of 4-nitroaniline with suitable electrophilic reagents, such as, but not limited to, acid chlorides, acid bromides, acid iodides, sulfonyl chlorides, isocyanates, carbonic acid anhydrides, activated esters, and alkyl haloformiates with or without the addition of bases, such as trialkyl amines, potassium carbonate, or lithium-, sodium-, or potassium alcoholates, in a suitable solvent, such as ethyl acetate, dioxane, tetrahydrofuran, acetonitrile or diethyl ether, at a suitable temperature, such as room temperature or reflux temperature, achieved by conventional heating or under microwave irradiation, followed by the reduction of the nitro group with a suitable reducing agent, such as sodium dithionite, iron or zinc powder in aqueous hydrochloric acid or hydrogen gas in the presence of a suitable hydrogenation catalyst such as palladium on activated carbon in suitable solvents such as methanol or ethanol, at a suitable temperature.

Compounds of the general formula V are prepared by the reaction of compounds of the general formula IV with a reagent forming a protecting group on the aniline group, for example phthalic anhydride, in a suitable solvent, such as glacial acetic acid, at a suitable temperature.

Compounds of the general formula VI are prepared from compounds of the general formula V by nitration reactions known to the chemist skilled in the art, such as reaction with fuming nitric acid, in a suitable solvent, such as glacial acetic acid, at a suitable temperature.

Compounds of the general formula VII are prepared from compounds of the general formula VI by deprotection of the aniline function with hydrazine hydrate in a suitable solvent, such as 1,2-dioxane, at a suitable temperature.

Alternatively, compounds of the general formula VII can be prepared from 2-nitro-1,4diaminobenzene in 3 steps as shown in the scheme and as described below. In the first step, the less hindered and the more reactive aniline nitrogen is protected with an appropriate protecting group PG [*Protective Groups in Organic Synthesis,* 3rd Edition T. W. Greene, P. G. M. Wuts, Wiley Interscience 1999] such as tert-butyloxycarbonyl group (a Boc group) by the reaction with the appropriate reagent forming protective group such as di-tert-butyl dicarbonate in an appropriate solvent such as acetonitrile and at appropriate temperature furnishing compounds of the general formula XI.

The compounds of the general formula XII are obtained from compounds of the general formula XI by the reaction with suitable electrophilic reagents forming $R^3$-$(Z)_q$-X group such as alkyl, aryl or heteroaryl chloroformiates or carbamoyl chlorides, acid chlorides, acid bromides, acid iodides, sulfonyl chlorides, isocyanates, carbonic acid anhydrides, activated carbonic acids with activating reagents such as carbodiimides or others as known to chemists skilled in the art, in suitable solvents, such as acetonitrile, tetrahydrofuran, 1,2-dichloroethane or methylene chloride at a suitable temperature, such as room temperature or reflux achieved by conventional heating or under microwave irradiation, with or without addition of bases, such as magnesium oxide, potassium carbonate, trialkylamines, pyridine or sodium hydrogencarbonate as descibed above for compounds of the general formula IV.

The protecting group is removed by the methods known to chemists skilled in the art. In particular, the Boc group can be cleaved by treatment with an appropriate acid, for example trifluoroacetic acid, in the absence or presence of solvent such as methylene chloride or toluene at the appropriate temperature furnishing compounds of the general formula VII.

Preparation of Compounds of the General Formula VIII:

Compounds of the general formula VII are subjected to reductive alkylation reactions, known to the chemist skilled in the art, with aldehydes of the general formulae IIa or IIIa, wherein $R^5$, W, m, n and p are as described above, using reducing agents, such as sodium borohydride or sodium cyanoborohydride in a suitable solvent, such as methanol, ethanol, tetrahydrofuran, water, dioxane or mixtures thereof, with or without addition of catalytic amounts of acid, such as acetic acid, at a suitable temperature, to form compounds of the general formula VIII, wherein $R^1$ is hydrogen.

Alternatively, compounds of the general structure VII can be reacted with aldehydes of the general structures IIa or IIIa in a suitable solvent, such as methanol, ethanol, tetrahydrofuran, dioxane, xylene, or mixtures thereof, with or without addition of catalytic amounts of acid, such as acetic acid or acidic ion exchange resin, at a suitable temperature, to form imines, that can be isolated by crystallisation or by evaporation of the solvent. The imines can then be reduced using reducing agents, such as sodium borohydride or sodium cyanoborohydride in a suitable solvent, such as methanol, ethanol, tetrahydrofuran, water, dioxane or mixtures thereof, to compounds of the general formula VIII, wherein $R^1$ is hydrogen.

Optionally, for variation of $R^1$, the obtained compounds of the general formula VIII can be subjected to an additional reductive alkylation procedure using suitable aldehydes and reducing agents, such as sodium borohydride or sodium cyanoborohydride in a suitable solvent, such as methanol, ethanol, tetrahydrofuran, water, dioxane or mixtures thereof, with or without addition of catalytic amounts of acid, such as acetic acid, at a suitable temperature as described above. This procedure can also be carried out in-situ after the first reductive alkylation with aldehydes of the general structures IIa or IIIa.

Alternatively, for variation of $R^1$, the obtained compounds of the general formula VIII can be subjected to an acylation reaction using suitable electrophilic reagents, such as acid chlorides, acid bromides, acid iodides, sulfonyl chlorides, and alkyl halo-formiates with the addition of bases, such as trialkyl amines, potassium carbonate, or lithium-, sodium-, or potassium alcoholates, in a suitable solvent, such as ethyl acetate, dioxane, tetrahydrofuran, or diethyl ether, at a suitable temperature, as described above.

Compounds of the general formula IX, are formed by reduction of compounds of the general formula VIII with a suitable reducing agent such as sodium dithionite, iron or zinc powder in aqueous hydrochloric acid or acetic acid in the absence or presence of organic solvents such as tetrahydrofuran or ethanol, or hydrogen gas in the presence of a suitable hydrogenation catalyst such as palladium on activated carbon in suitable solvents such as methanol or ethanol or water/tetrahydrofuran mixture, at an suitable temperature. The resulting compounds are identical to compounds of the invention of the general formula I, wherein $R^2$ and $R^{2'}$ are hydrogen, and wherein $R^1$, $R^3$, X, Y, Z, and q are as defined above.

Compounds of the general formula I, wherein $R^1$ is not hydrogen, and where $R^2$ and optionally $R^{2'}$ are not hydrogen, are obtained by the reaction of compounds of the general formula IX, wherein $R^1$ is not hydrogen, by using the following methods:

Introduction of $R^2$ by a reductive alkylation procedure using suitable aldehydes and reducing agents, such as sodium borohydride or sodium cyanoborohydride in a suitable solvent, such as methanol, ethanol, tetrahydrofuran, water, dioxane or mixtures thereof, with or without addition of catalytic amounts of acid, such as acetic acid, at a suitable temperature, as described above.

Optional introduction of $R^{2'}$ by an additional reductive alkylation procedure using suitable aldehydes and reducing agents, such as sodium borohydride or sodium cyanoborohydride in a suitable solvent, such as methanol, ethanol, tetrahydrofuran, water, dioxane or mixtures thereof, with or without addition of catalytic amounts of acid, such as acetic acid, at a suitable temperature, as described above.

Alternatively, $R^{2'}$ or $R^2$ is introduced by an acylation reaction using suitable electrophilic reagents, such as acid chlorides, acid bromides, acid iodides, sulfonyl chlorides, and alkyl halo-formiates with the addition of bases, such as trialkyl amines, potassium carbonate, or lithium-, sodium-, or potassium alcoholates, in a suitable solvent, such as ethyl acetate, dioxane, tetrahydrofuran, or diethyl ether, at a suitable temperature, as described above.

To obtain compounds of the general formula I, where $R^1$ is hydrogen, and where $R^2$ and optionally $R^{2'}$ is not hydrogen, a protecting group, such as tert-butyloxycarbonyl is introduced as $R^1$ before the reduction of the nitro group, by methods known to the chemist skilled in the art. This protecting group is cleaved after the introduction of $R^2$ and optionally $R^{2'}$ by known methods.

Compounds of the general formulae IIa and IIIa are prepared, by standard methods known to chemists skilled in the art as outlined below:

Reduction of a carboxylic acid ester with an appropriate reducing agent, such as diisobutyl aluminium hydride, followed by oxidation of the resulting benzylic alcohol with a suitable oxidant, such as tetrapropylammonium perruthenate/N-methylmorpholin-N-oxide, pyridinium chlorochromate, dimethylsulfoxide/oxalylchloride. Alternatively, compounds of the general formulae IIa and IIIa can be prepared by formylation reactions with dichloromethyl metyl ether and titanium tetrachloride (Gross et al, *Org. Synth. Coll*, 1973 Vol V, 365; Fanghaenel et al. *J. Prakt. Chem.* 1997, 339, 277). Alternatively, compounds of the general formulae II and IIIa can be prepared by methods known to chemists skilled in the art, such as deprotonation of a heteroaromatic compound with a strong base, such as alkyllithium, and subsequent reaction with N,N-dimethylformamide. Alternatively, compounds of the general formulae IIa and IIIa can be prepared by methods known to chemists skilled in the art, such as halogen metal exchange reaction of halogen substituted heteroaromatic compounds, such as bromides or iodides, by the reaction with a metalating reagent, such as alkyllithium or alkylmagnesium halide or dialkylmagnesium. Alternatively, compounds of the general formulae IIa and IIIa can be prepared by methods known to chemists skilled in the art, such as reaction of thiophenes and benzothiophenes with phosphoryl chloride in the presence of N-methyl-N-phenyl formamide (King et al. *J. Org. Chem.* 1949, 14, 638) or N,N-dimethylformamide (Vilsmeier formylation, Raimundo et al. *J. Org Chem.* 2002, 67, 205).

EXAMPLES

Analytical LC-MS data were obtained on a PE Sciex API 150EX instrument equipped with IonSpray source and Shimadzu LC-8A/SLC-10A LC system. Column: 30×4.6 mm Waters Symmetry C18 column with 3.5 μm particle size; Solventsystem: A=water/trifluoroacetic acid (100:0.05) and B=water/acetonitrile/trifluoroacetic acid (5:95:0.03); Method: Linear gradient elution with 90% A to 100% B in 4 minutes and with a flow rate of 2 mL/min. Purity was determined by integration of the UV (254 nm) and ELSD trace. The retention times (RT or $t_R$) are expressed in minutes.

Preparative LC-MS-purification was performed on the same instrument. Column: 50×20 mm YMC ODS-A with 5 μm particle size; Method: Linear gradient elution with 80% A to 100% B in 7 minutes and with a flow rate of 22.7 mL/min. Fraction collection was performed by split-flow MS detection.

$^1$H NMR spectra were recorded at 500.13 MHz on a Bruker Avance DRX500 instrument or at 250.13 MHz on a Bruker AC 250 instrument. Deuterated chloroform (99.8% D) or dimethyl sulfoxide (99.8% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, ddd=double double doublet, dt=double triplet, dq=double quartet, tt=triplet of triplets, m=multiplet and b=broad singlet. In certain cases, coupling constants, J, are given. Melting points (M.p.) were recorded on a Buichi B-540 apparatus and are uncorrected.

Preparation of Intermediates (4-Amino-phenyl)-carbamic acid ethyl ester

4-Nitro-aniline (100 g, 0.72 mol) is dissolved in ethyl acetate (800 mL) and diisopropylethylamine (89.6 mL, 0.936 mol) is added. Ethyl chloroformiate (252 mL, 1.45 mol) dissolved in ethyl acetate (200 mL) is added and the solution is stirred for 18 h at ambient temperature. The mixture is washed with 2M HCl (300 mL) and brine (300 mL), dried (MgSO$_4$) and concentrated in vacuo to half of the original volume. To the resulting solution is added palladium on activated carbon (10 g, 5% Pd, 50% H$_2$O) and the mixture is hydrogenated on a Parr apparatus (pH$_2$=3 bar) at ambient temperature for 12 hours. The mixture is filtered through Celite and the solvent evaporated in vacuo to give 118 g (90%) of the title compound as crystalline product. LC/MS (m/z) 180.9 (MH$^+$); $t_R$=0.60 min. $^1$H NMR (CDCl$_3$): 1.27 (t, 3H); 3.42 (b, 2H, NH$_2$); 4.19 (q, 2H); 6.52 (b, 1H NH); 6.64 (m, 2H); 7.14 (m, 2H).

The following compound was prepared in an analogous fashion:

(4-Amino-phenyl)-carbamic acid propyl ester

Yield: 98%. $^1$H NMR (CDCl$_3$): 0.96 (t, 3H); 1.68 (m, 2H); 3.51 (b, 2H); 4.09 (t, 2H); 6.46 (b, 1H); 6.63 (d, 2H); 7.14 (m, 2H).

(4-Phtalimido-phenyl)-carbamic acid ethyl ester (4-Amino-phenyl)-carbamic acid ethyl ester (118 g, 0.65 mol) is dissolved in glacial acetic acid (2.0 L) under nitrogen and the mixture is heated to 90° C. Phthalic anhydride (102.0 g, 0.69 mol) is added portionwise over 30 minutes and the reaction is kept at 90° C. for 2 hours. The mixture is allowed to cool to ambient temperature and the precipitated solid is filtered off. The solid is washed on the filter with water (2 L) followed by diethylether (3 L) and then dried in vacuo. Yield 127 g (62%) title compound as white crystalline compound. LC/MS (m/z) 311.3 (MH$^+$); $t_R$=2.57 min. $^1$H NMR (DMSO-d$_6$): 1.26 (t, 3H); 4.15 (q, 2H); 7.34 (dd, 2H); 7.58 (dd, 2H); 7.90 (ddd, 2H); 7.95 (ddd, 2H); 9.80 (s, 1H, NH).

The following compound was prepared in an analogous fashion:

(4-Phtalimido-phenyl)-carbamic acidpropyl ester

Yield: 81%.

(2-Nitro-4-phtalimido-phenyl)-carbamic acid ethyl ester (4-Phtalimido-phenyl)-carbamic acid ethyl ester (99.0 g, 0.32 mol) is suspended in glacial acetic acid (1.5 L) and heated to 90° C. Fuming nitric acid (17.2 mL, 0.41 mol) is added dropwise over 30 minutes at 90-95° C. The reaction mixture is then stirred at 100° C. for 1 hour and cooled to ambient temperature. Crystallised solids are filtered off and washed with glacial acetic acid (500 mL), water (1 L) and diethylether (1 L) on the filter, then dried in vacuo to furnish 101 g (90%) of the title compound as a yellow solid. LC/MS (m/z) 355.0 (MH$^+$); $t_R$=3.34 min. $^1$H NMR (DMSO-d$_6$): 1.25 (t, 3H); 4.16 (q, 2H); 7.81 (m, 2H); 7.93 (ddd, 2H); 7.99 (ddd, 2H); 6.15 (dd, 1H); 9.99 (s, 1H, NH).

The following compound was prepared in an analogous fashion:

(2-Nitro-4-phtalimido-phenyl)-carbamic acidpropyl ester

Yield: 70%.

(4-Amino-2-nitro-phenyl)-carbamic acid ethyl ester 1,2-Dimethoxyethane (1.0 L) is added to (2-nitro4-phtalimido-phenyl)-carbamic acid ethyl ester (101 g, 0.28 mol) and the mixture is heated under reflux. Hydrazine monohydrate (19.6 g, 0.39 mol) is added dropwise over 10 minutes and the mixture is stirred at reflux for 1.5 hours. Upon cooling to ambient temperature the mixture is filtered and the solids are washed with dimethoxyethane (250 mL) on the filter. The filtrate is concentrated by means of evaporation and the red crystalline product is recrystallized from toluene (350 mL), precipitated product is filtered off and dried in vacuo. The mother liquor is concentrated to half the original volume and left standing for 16 hours. Precipitated material is filtered off and recrystallized as before. The recrystallized solids are combined to furnish a total of 57.6 g (90%) dark red title compound. LC/MS (m/z) 225.1 ($MH^+$); $t_R$=2.08 min. $^1$H NMR (CDCl$_3$): 1.33 (t, 3H); 3.77 (s, 2H, NH$_2$); 4.23 (q, 2H); 6.98 (dd, 1H); 7.45 (d, 1H); 8.28 (d, 1H); 9.39 (s, 1H, NH).

The following compound was prepared in an analogous fashion:

(4-amino-2-nitro-phenyl)-carbamic acid propyl ester

Yield: 91%. $^1$H NMR (CDCl$_3$): 0.98 (t, 3H); 1.71 (m, 2H); 3.78 (b, 2H); 4.13 (t, 2H); 6.98 (dd, 1H); 7.44 (d, 1H); 8.27 (d, 1H); 9.39 (s, 1H).

(4-Amino-3-nitro-phenyl)-carbamic acid tert-butyl ester

To a refluxing solution of 2-nitro-1,4-diaminobenzene (10.135 g, 66.18 mmol) in tetrahydrofuran (100 mL) Boc$_2$O (di-tert-butyl dicarbonate, 32.6 g, 149 mmol) was added by portions during 2 hours. The obtained solution was poured into heptane (2 L), sonicated for 15 minutes, filtered and dried in vacu to furnish 13.40 g of the title compound as a red solid. Yield 80%. LC/MS (m/z) 295.4 ($[M+H+MeCN]^+$); $t_R$=2.54 (UV, ELSD) 96%, 100%. $^1$H NMR (DMSO-d$_6$): 1.47 (s, 9H); 6.96 (d, 1H); 7.24 (s, 2H, NH$_2$), 7.41 (dd, 1H); 8.20 (s, 1H); 9.28 (s, 1H, NH).

[4-(4-Chloro-benzenesulfonyl)-3-methyl-thiophen-2-yl]-methanol

A solution of 4-(4-Chloro-benzenesulfonyl)-3-methyl-thiophene-2-carboxylic acid methyl ester (992 mg, 3.00 mmol) in dry tetrahydrofuran (20 mL) and dry CH$_2$Cl$_2$ (10 mL) was cooled to 0° C. under N$_2$, and DIBAL-H (9.0 mL, 9.0 mmol, 1 M solution in toluene) was added. After 3 hours, another portion of DIBAL-H (4.5 mL, 4.5 mmol) was added, and stirring was continued for another 2 hours. The reaction was quenched by the addition of saturated Rochelle salt solution (30 mL), and the mixture was stirred for 1 hour at room temperature. The phases were separated, the aqueous phase was extracted with EtOAc (2×50 mL) and the pooled organic layers were dried over Na$_2$SO$_4$ and evaporated in vacuo. The product was purified by chromatography on silica gel on a FlashMaster system using as eluent heptane/ethyl acetate (linear gradient elution from 1:0 to 6:4). Fractions containing the product were pooled and evaporated in vacuo to yield the desired compound (788 mg, 87%). LC-MS: (m/z)=285.2 ($M-H_2O+H^+$), calcd for C$_{12}$H$_{10}$ClO$_2$S$_2$: 284.9805, $t_R$=2.45 min. $^1$H NMR (CDCl$_3$): 1.84 (t, J=5.7 Hz, 1 H), 2.20 (s, 3 H), 4.73 (d, J=5.7 Hz, 2 H), 7.49 (d, J=8.5 Hz, 2 H), 7.84 (d, J=8.5 Hz, 2 H), 8.18 (s, 1 H).

The following compounds were prepared analogously:

(3-Chloro-thiophen-2-yl)-methanol

Yield: 73%. $^1$H NMR (CDCl$_3$): 1.92 (b, 1 H), 4.81 (s, 2 H), 6.91 (d, J=5.2 Hz, 1 H), 7.25 (d, J=5.2 Hz, 1 H).

(5-Dimethylamino-benzo[b]thiophen-3-yl)-methanol

Yield: 63%. $^1$H NMR (CDCl$_3$): 1.62 (b, 1 H), 3.01 (s, 6 H), 4.89 (s, 2 H), 6.96 (dd, 1 H), 7.11 (d, 1 H), 7.34 (s, 1 H), 7.68, (d, J=9.0 Hz, 1 H).

(5-Dimethylamino-3-methyl-benzo[b]thiophen-2-yl)-methanol

Yield: 56%. $^1$H NMR (CDCl$_3$): 1.69 (t, J=5.9 Hz, 1 H), 2.35 (s, 3 H), 3.00 (s, 6 H), 4.88 (d, 2 H), 6.90 (d, 1 H), 6.93 (dd, 1 H), 7.63, (d, 1 H).

(4-Bromo-3-methoxy-thiophen-2-yl)-methanol

A suspension of 4-bromo-3-hydroxy-thiophene-2-carboxylic acid methyl ester (948 mg, 4.00 mmol), dimethyl sulphate (0.57 mL, 6.0 mmol), and K$_2$CO$_3$ (1.11 g, 8.0 mmol) in acetone (10 mL) was heated under reflux for 4 hours. After cooling to room temperature, water (25 mL) was added. The mixture was extracted with EtOAc (2×25 mL), and the extracts were pooled, dried over Na$_2$SO$_4$, and evaporated in vacuo. The residue was dissolved in dry tetrahydrofuran (20 mL), the solution was cooled to 0° C. under N$_2$, and DIBAL-H (12 mL, 12 mmol, 1 M solution in toluene) was added.

After 2 hours, another portion of DIBAL-H (6 mL, 6 mmol) was added, and stirring was continued for another 2 hours. The reaction was quenched by the addition of saturated Rochelle salt solution (30 mL), and the mixture was stirred for 1 hour at room temperature. The phases were separated, the aqueous phase was extracted with EtOAc (2×50 mL) and the pooled organic layers were dried over Na$_2$SO$_4$ and evaporated in vacuo. The product was purified by chromatography on silica gel on a FlashMaster system using as eluent heptane/ethyl acetate (linear gradient elution from 1:0 to 2:1). Fractions containing the product were pooled and evaporated in vacuo to yield the desired compound (482 mg, 54%). $^1$H NMR (CDCl$_3$): 1.86 (b, 1 H), 3.90 (s, 3 H), 4.77 (s, 2 H), 7.15 (s, 1 H).

The following compound was prepared analogously:

(6-Chloro-3-methoxy-benzo[b]thiophen-2-yl)-methanol

Yield: 75%. $^1$H NMR (CDCl$_3$): 1.92 (t, J=5.9 Hz, 1 H), 3.99 (s, 3 H), 4.90 (d, J=5.7 Hz, 2 H), 7.33 (dd, J=1.9, 8.5 Hz, 1 H), 7.64 (d, J=8.5 Hz, 1 H), 7.73 (d, J=1.9 Hz, 1 H).

Preparation of Heteroaryl Aldehydes of the General Formula IIa and IIIa 4-(4-Chloro-benzenesulfonyl)-3-methyl-thiophene-2-carbaldehyde To a suspension of [4-(4-chloro-benzenesulfonyl)-3-methyl-thiophen-2-yl]-methanol (786 mg, 2.60 mmol), 4-methylmorpholine N-oxide (0.46 g, 3.9 mmol), and powdered 4 Å molecular sieves (1.3 g, activated by brief heating in vacuo) in $CH_2Cl_2$ (7 mL) was added tetrapropylammonium perruthenate (46 mg, 0.13 mmol). The resulting mixture was stirred for 1 hour, after which it was filtered through a plug of silica (ca. 25 g) eluting with EtOAc. The eluate was evaporated in vacuo and the product was purified by chromatography on silica gel on a FlashMaster system using as eluent heptane/ethyl acetate (linear gradient elution from 1:0 to 1:1). Fractions containing the product were pooled and evaporated in vacuo to yield the title compound (644 mg, 82%). $^1$H NMR ($CDCl_3$): 2.60 (s, 3 H), 7.53 (d, J=9.0 Hz, 2 H), 7.87 (d, J=8.5 Hz, 2 H), 8.53 (s, 1 H), 10.01 (s, 1 H).

The following aldehydes were prepared analogously:

3-Chloro-thiophene-2-carbaldehyde

Yield: 94%. $^1$H NMR ($CDCl_3$): 7.07 (d, J=5.2 Hz, 1 H), 7.72 (d, J=0.5, 4.7 Hz, 1 H), 10.07 (d, J=0.9 Hz, 1 H).

4-Bromo-3-methoxy-thiophene-2-carbaldehyde

Yield: 45%. $^1$H NMR ($CDCl_3$): 4.18 (s, 3 H), 7.60 (d, J=1.4 Hz, 1 H), 10.08 (d, J=1.4 Hz, 1 H).

6-Chloro-3-methoxy-benzo[b]thiophene-2-carbaldehyde

Yield: 86%. $^1$H NMR ($CDCl_3$): 4.34 (s, 3 H), 7.36 (dd, J=1.7, 8.7 Hz, 1 H), 7.75 (d, J=1.4 Hz, 1 H), 7.82 (d, J=8.5 Hz, 1 H), 10.36 (s, 1 H).

5-Dimethylamino-benzo[b]thiophene-3-carbaldehyde

Yield: 72%. $^1$H NMR ($CDCl_3$): 3.05 (s, 6 H), 7.00 (dd, J=2.4, 9.0 Hz, 1 H), 7.68 (d, J=9.0 Hz, 1 H), 7.99 (d, J=2.8 Hz, 1 H), 8.24 (s, 1 H), 10.11 (s, 1 H).

5-Dimethylamino-3-methyl-benzo[b]thiophene-2-carbaldehyde

Yield: 73%. $^1$H NMR ($CDCl_3$): 2.74 (s, 3 H), 3.03 (s, 6 H), 7.00 (d, J=2.4 Hz, 1 H), 7.12 (dd, J=2.4, 9.0 Hz, 1 H), 7.69 (d, J=9.0 Hz, 1 H), 10.30 (s, 1 H).

5-Fluoro-benzofuran-3-carbaldehyde

At a constant temperature of −60° C. dimethylsulfoxide (3.27 g, 41.8 mmol) in dichloromethane (10 mL) was added to a solution of oxalylchloride (2.65 g, 20.9 mmol) in dichloromethane (30 mL) and the solution was stirred for 15 minutes. 1-(5-Fluorobenzofuran-3-yl)methanol (3.16 g, 19.0 mmol) dissolved in dichloromethane (60 mL) was added dropwise at −60° C. The mixture was stirred for 20 minutes followed by addition of triethylamine (9.61 g, 0.095 mmol). After stirring for 10 minutes, the reaction mixture was allowed to heat to ambient temperature and stirred for additional 20 minutes. The organic fraction was washed successively with 50 mL portions of water, 1N aqueous HCl, saturated aqueous sodium bicarbonate and brine, then dried ($MgSO_4$) and concentrated in vacuo to furnish crude title compound in quantitative yield as a beige crystalline solid. $^1$H NMR ($CDCl_3$): 7.13 (dt, 1H); 7.50 (dd, 1H); 7.86 (dd, 1H); 8.30 (s, 1H); 10.15 (s, 1H).

5-Fluoro-thiophene-2-carbaldehyde

To a solution of thiophene (4.8 mL, 60 mmol) in dry $Et_2O$ (200 mL) at 0° C. was added n-BuLi (70 mL, 66 mmol, 0.95 M in hexane) dropwise, and the solution was stirred for 1 hour at −5-0° C. Then the temperature was adjusted to −70° C., and a solution of $(PhSO_2)_2NF$ (28.4 g, 90 mmol) in dry tetrahydrofuran (200 mL) was added, while maintaining the temperature below −50° C. The resultant mixture was then slowly allowed to warm to room temperature overnight, 2 N NaOH (300 mL) was added, the mixture was filtered, and the organic layer was washed with 2 N NaOH (2×300 mL) and saturated $NH_4Cl$ (300 mL) and was then dried over $Na_2SO_4$. Distillation using a 40 cm Vigreux column removed most of the $Et_2O$, and final co-distillation with heptane (50 mL) yielded a solution of 20.7 mmol 2-fluorothiophene and 4.6 mmol thiophene (determined by $^1$H NMR using 200 µL of DME as internal standard) in ca. 100 mL of tetrahydrofuran and heptane (bp. 60-100° C.). This solution was cooled to 0° C. and n-BuLi (44 mL, 41 mmol, 0.95 M in hexane) was added dropwise. After 1 hour, a solution of DMF (4.8 mL, 62 mmol) in $Et_2O$ (15 mL) was added dropwise, and stirring was continued for another 1 hour at 0° C. The reaction was then quenched with saturated $NH_4Cl$ (200 mL) and extracted with $Et_2O$ (2×200 mL), and the extract was dried over $Na_2SO_4$. Most of the solvent was removed by distillation at atmospheric pressure (40 cm Vigreux column) and the dark residue was then vacuum distilled to yield a ca 10:1 mixture of 5-fluoro-thiophene-2-carbaldehyde and thiophene-2-carbaldehyde (bp. 78-79° C., 25 mmHg) as a golden oil (1.32 g, 44%). This mixture was used without further purification. $^1$H NMR ($CDCl_3$): 6.65 (d, J=4.2, 1 H), 7.50 (d, J=3.8 Hz, 1 H), 9.76 (d, J=4.2 Hz, 1 H).

Preparation of Intermediates of General Formula VII

Intermediates of the general formula VII were prepared by a general method as described below for the preparation of {4-[(5-Fluoro-benzofuran-3-ylmethyl)-amino]-2-nitro-phenyl}-carbamic acid ethyl ester, or by a general method as described below for the preparation of N-(4-Amino-2-nitro-phenyl)-2-(4-fluorophenyl)acetamide.

{4-[(5-Fluoro-benzofuran-3-ylmethyl)-amino]-2-nitro-phenyl}-carbamic acid ethyl ester In a 3-necked round bottomed flask fitted with a Dean-Stark apparatus 5-Fluoro-benzofuran-3-carbaldehyde (3.59 g, 21.9 mmol) and (4-amino-2-nitro-phenyl)-carbamic acid ethyl ester (4.48 g, 19.9 mmol) were mixed in o-xylene (80 mL) and a catalytic amount of acidic ion exchange resin (Amberlite IRC-84, 100 mg) was added. The mixture was heated to reflux for 5 hours, filtered warm and concentrated in vacuo. This crude product was dissolved in a dioxane: methanol (4:1) mixture (90 mL) and sodiumborohydride (1.50 g, 39.8 mmol) was added portionwise over a period of 30 minutes. The reaction mixture was stirred at ambient temperature over night, then poured into water (200 mL) and extracted with ethyl acetate (3×75 mL). The combined organic fractions were washed with brine, dried ($MgSO_4$) and evaporated to give a crude solid which was purified by chromatography on silica gel (eluent:ethyl acetate:heptane 1:2). This furnished 4.50 g (61%) of the title compound as a red crystalline material. $^1$H NMR (CDCl3): 1.33 (t, 3H); 4.07 (t, 1H); 4.23 (q, 2H); 4.42 (d, 2H); 6.99 (dd, 1H); 7.05 (dt, 1H); 7.25 (dd, 1H); 7.42 (t, 1H); 7.44 (d, 1H); 7.65 (s, 1H); 8.31 (d, 1H); 9.39 (s, 1H).

The following intermediates were prepared analogously:

{4-[(5-Methyl-thiophen-2-ylmethyl)-amino]-2-nitro-phenyl}-carbamic acid ethyl ester Yield: 73%. LC/MS (m/z) 336 (MH$^+$); $t_R$=3.41 min.

{4-[(3-Methyl-thiophen-2-ylmethyl)-amino]-2-nitro-phenyl}-carbamic acid ethyl ester Yield: 89%. LC/MS (m/z)

{4-[(Thiophen-2-ylmethyl)-amino]-2-nitro-phenyl}-carbamic acid ethyl ester

Yield: 71%. LC/MS (m/z) 321 (MH$^+$); $t_R$=3.24 min.

{4-[(Thiophen-3-ylmethyl)-amino]-2-nitro-phenyl}-carbamic acid ethyl ester

Yield: 69%. LC/MS (m/z) 320 (MH$^+$); $t_R$=3.08 min.

{4-(Benzo[b]thiophen-3-ylmethyl)-amino]-2-nitro-phenyl}-carbamic acid ethyl ester Yield: 87%. M.p. 151-152° C. LC-MS (m/z) 371.0 (MH$^+$), $t_R$=3.59 min.

N-(4-Amino-2-nitrophenyl)-2-(4-fluorophenyl)aceta-mide

To a stirred suspension of {4-[2-(4-fluorophenyl)-acety-lamino]-3-nitro-phenyl}-carbamic acid tert-butyl ester (2.40 g, 6.16 mmol) in methylene chloride (5 mL) trifluoroacetic acid (5 mL) was added. After 15 minutes methylene chloride was distilled off and the residual solution was transferred into saturated aqueous NaHCO$_3$ solution (200 mL) with sonication. The precipitate was filtered, washed with water and dried in vacuo to furnish 1.70 g of the title compound as a red-brown solid. Yield 96.3%. LC/MS; $t_R$=2.25 (UV, ELSD) 89%, 100%. $^1$H NMR (DMSO-d$_6$): 3.59 (s, 2H); 5.65 (b, 2H, NH$_2$); 6.83 (dd, 1H); 7.08 (d, 1H); 7.15 (t, 2H), 7.21 (d, 1H); 7.32 (dd, 2H); 9.91 (s, 1H, NH).

The following compound was prepared analogously:

N-(4-Amino-2-nitrophenyl)-3,3-dimethylbutyramide

Yield 680 mg, 93%. LC/MS (m/z) 293.43 ([M+H+MeCN]$^+$); $t_R$=2.29 (UV, ELSD) 99.5%, 99.1%. 1H NMR (DMSO-d$_6$): 1.00 (s, 9H); 2.12 (s, 2H); 3.45 (b, H$_2$O+NH$_2$); 6.84 (dd, 1H); 7.06 (d, 1H); 7.14 (d, 1H); 9.64 (s, 1H, NH).

Preparation of Intermediates of the General Formula VIII

N-{4-[(5-Chlorothiophen-2-ylmethyl)amino]-2-ni-trophenyl}-2-(4-fluorophenyl)acetamide A solution of N-(4-amino-2-nitrophenyl)-2-(4-fluorophe-nyl)acetamide (306 mg, 1.06 mmol) and 5-chloro-2-thiophenecarboxaldehyde (186 mg, 1.2 eq.) in anhydrous ethanol (40 mL) was heated at 70° C. for 30 minutes. The obtained solution was concentrated to a small volume (ca. 3 mL) and quenched with heptane (15 mL). The brown crystalline product was separated by filtration to furnish 350 mg of intermediate imine N-{4-[(5-chlorothiophen-2-ylm-ethylene)amino]-2-nitrophenyl}-2-(4-fluorophenyl)aceta-mide. Yield 79.2%. $^1$H NMR (DMSO-d$_6$): 3.71 (s, 2H); 7.17 (t, 2H); 7.29 (d, 1H); 7.36 (dd, 2H); 7.62 (d, 1H); 7.63 (dd, 1H); 7.71 (d, 1H); 8.83 (s, 1H); 10.44 (s, 1H). The solid was suspended in methanol (5 mL), NaBH$_3$CN (200 mg) was added followed by acetic acid (2 mL). The obtained solution turned into a suspension. After 15 minutes it was treated with water (50 mL) and the product was separated by filtration to furnish 330 mg of red solid after drying in vacuo. Yield 93.8%. LC/MS (m/z) 420 ([M+H]$^+$); $t_R$=3.34 (UV, BLSD) 97%, 100%. $^1$H NMR (DMSO-d$_6$): 3.60 (s, 2H); 4.45 (d, 2H); 6.87 (t, 1H, NH); 6.93 (dd, 1H); 6.94 (d, 1H); 6.97 (d, 1H); 7.11 (d, 1H); 7.14 (t, 2H); 7.28 (d, 1H); 7.32 (dd, 2H); 9.98 (s, 1H).

The following compound was prepared analogously from the corresponding aniline:

N-{4-[(5-Chlorothiophen-2-ylmethyl)amino]-2-ni-trophenyl}-3,3-dimethylbutyramide The crude intermediate imine was separated by evapora-tion and reduced as described above. Then, the reaction mixture was evaporated to a small volume, treated with saturated aqueous NaHCO$_3$ and ethyl acetate and the organic layer was evaporated. The residue was dissolved in hot diisopropyl ether, precipitated with heptane and filtered. Yield 880 mg, 87.6%. LC/MS (m/z) 382.48 ([M+H]$^+$); $t_R$=3.46 (UV, ELSD) 88%, 91%. $^1$H NMR (DMSO-d$_6$): 0.99 (s, 9H); 2.12 (s, 2H); 4.45 (d, 2H); 6.84 (t, 1H, NH); 6.92 (dd, 1H); 6.94 (d, 1H); 6.97 (d, 1H); 7.07 (d, 1H); 7.19 (d, 1H); 9.69 (s, 1H).

Preparation of Intermediates of the General Formula XII

{4-[2-(4-Fluorophenyl)acetylamino]-3-nitrophenyl}carbamic acid tert-butyl ester

To a suspension of (4-amino-3-nitrophenyl)-carbamic acid tert-butyl ester (1.992 g, 7.87 mmol) and NaHCO$_3$ (5.4 g) in acetonitrile (20 mL) (4-fluorophenyl)acetyl chloride was added (1.8 mL, 1.3 eq.). The obtained suspension was sonicated for 5 minutes and stirred at ambient temperature for 16 hrs. It was poured into water (200 mL), sonicated for 5 minutes, filtered, and washed with water and heptane. The obtained residue was dissolved in hot ethyl acetate (30 mL), saturated aqueous NaHCO$_3$ was added (50 mL) and the obtained mixture was quenched with heptane (200 mL). The obtained suspension was sonicated for 5 minutes and fil-tered. The residue was washed with water and heptane and dried in vacuo to furnish 2.48 g of a brown-yellow solid. Yield 80.9%. LC/MS (m/z) 412.54 ([M+Na]$^+$), 453.58 ([M+MeCN+Na]$^+$); $t_R$=3.33 (UV, ELSD) 97%, 100%. $^1$H NMR (DMSO-d$_6$): 1.48 (s, 9H); 3.66 (s, 2H); 7.16 (t, 2H), 7.34 (dd, 2H); 7.54 (d, 1H); 7.64 (dd, 1H); 8.16 (d, 1H); 9.79 (s, 1H, NH), 10.29 (s, 1H, NH).

The following compound was prepared analogously using the corresponding acid chloride:

[4-(3,3-Dimethylbutyrylamino)-3-nitrophenyl]car-bamic acid tert-butyl ester

The reaction mixture was stirred at 45° C. for 30 minutes with an excess of tert-butylacetyl chloride (3 eq.). The crude product was separated after ethyl acetate—saturated aque-ous NaHCO$_3$ work-up and purified by flash chromatography on SiO$_2$ (50 g) with 10-15% ethyl acetate—heptane as an eluent. Yield 2.20 g (78.6%), yellow solid. LC/MS (m/z) 415.58 ([M+MeCN+Na]$^+$); $t_R$=3.31 (UV, ELSD) 99.5%, 99.9%. $^1$H NMR (DMSO-d$_6$): 1.01 (s, 9H); 1.49 (s, 9H); 2.17 (s, 2H); 7.43 (d, 2H); 7.63 (dd, 1H); 8.11 (d, 1H); 9.77 (s, 1H, NH); 10.01 (s, 1H, NH).

Compounds of the Invention

Acid addition salts of the compounds of the invention may easily be formed by methods known to the person skilled in the art.

Example 1

1a {2-Amino-4-[(5-fluoro-benzofuran-3-ylmethyl)-amino]-phenyl}-carbamic acid ethyl ester {4-[(5-Fluoro-benzofuran-3-ylmethyl)-amino]-2-nitro-phenyl}-carbamic acid ethyl ester (4.50 g, 12.1 mmol) was dissolved in absolute ethanol (140 mL) whereto 6N aqueous HCl (38 mL) and iron powder (5.70 g, 0.10 mol) was added. The red mixture was heated at 60° C. until the intense colour disappeared (20 minutes). The solids were filtered off and the ethanol was removed from the filtrate by evaporation in vacuo. Aqueous ammonia (saturated) was added to the remanence, which was then extracted with ethyl acetate (3×100 mL). The combined organic fractions were washed with brine, dried (MgSO$_4$) and concentrated in vacuo. The crude product was purified by chromatography on silica gel (eluent:ethyl acetate:heptane 1:1) to furnish 2.70 g (66%) of the title compound as a solid. M.p. 150-151° C. Calculated for C$_{18}$H$_{18}$FN$_3$O$_3$: C, 62.96; H, 5.28; N, 12.24. Found: C, 63.00; H, 5.38; N, 12.13. LC/MS (m/z) 344 (MH$^+$); $t_R$=2.00 min. $^1$H NMR (DMSO-d$_6$): 1.19 (t, 3H); 4.03 (q, 2H); 4.26 (d, 2H); 4.55 (s, 2H, NH2); 5.79 (t, 1H); 5.91 (dd, 1H); 6.02 (d, 1H, NH); 6.72 (d, 1H); 7.13 (dt, 1H); 7.56 (m, 2H); 7.95 (s, 1H); 8.16 (b, 1H, NH).

The following compounds were prepared analogously and isolated as their hydrochloric acid addition salts:

1b {2-Amino-4-[(5-methyl-thiophen-2-ylmethyl)-amino]-phenyl}-carbamic acid ethyl ester dihydrochloride Precipitation of the crude product from ethyl acetate by addition of ethereal hydrochloric acid gave the title compound.

M.p. 190° C. (dec.). Calculated for C$_{15}$H$_{19}$N$_3$O$_2$S,2HCl: C, 47.00; H 5.67; N, 10.97. Found: C, 46.84; H, 5.86; N, 11.10. LC/MS (m/z) 306 (MH$^+$); $t_R$=1.77 min. $^1$H NMR (DMSO-d$_6$): 1.22 (t, 3H); 2.37 (s, 3H); 4.08 (q, 2H); 4.37 (s, 2H); 6.64 (m, 1H); 6.67 (dd, 1H); 6.72 (d, 1H); 6.86 (d, 1H); 7.13 (d, 1H); 8.93 (b, 1H, NH).

1c {2-Amino-4-[(3-methyl-thiophen-2-ylmethyl)-amino]-phenyl}-carbamic acid ethyl ester dihydrochloride Precipitation of the crude product from ethyl acetate by addition of ethereal hydrochloric acid gave the title compound.

LC/MS (m/z) 306 (MH$^+$); $t_R$=1.68 min. $^1$H NMR (CDCl$_3$) (free base): 1.25 (t, 3H); 2.23 (s, 3H); 3.78 (b, 3H); 4.13 (q, 2H); 4.32 (s, 2H); 6.05-6.10 (m, 2H+NH); 6.82 (d, 1H); 6.93 (d, 1H); 7.11 (d, 1H).

1d {2-Amino-4-[(thiophen-2-ylmethyl)-amino]-phenyl}-carbamic acid ethyl ester dihydrochloride Precipitation of the crude product from ethanol by addition of ethereal hydrochloric acid gave the title compound.

M.p. 195° C. Calculated for C$_{14}$H$_{17}$N$_3$O$_2$S,2HCl: C, 46.16; H, 5.26; N, 11.54. Found: C 46.34; H, 5.43; N, 11.28. LC/MS (m/z) 292 (MH$^+$); $t_R$=1.58 min. $^1$H NMR (DMSO-d$_6$): 1.22 (t, 3H); 4.08 (q, 2H); 4.48 (s, 2H); 6.71 (dd, 1H); 6.79 (d, 1H); 7.10 (d, 1H); 7.16 (d, 1H); 7.40 (d, 1H); 8.97 (b, 1H, NH).

1e {2-Amino-4-[(thiophen-3-ylmethyl)-amino]-phenyl}-carbamic acid ethyl ester dihydrochloride Precipitation of the crude product from ethyl acetate by addition of ethereal hydrochloric acid gave the title compound.

M.p. 196-197° C. Calculated for C$_{14}$H$_{17}$N$_3$O$_2$S,2HCl: C, 46.16; H, 5.26; N, 11.54. Found: C, 46.23; H, 5.47; N, 11.30. LC/MS (m/z) 292 (MH$^+$); $t_R$=1.54 min. $^1$H NMR (DMSO-d$_6$): 1.21 (t, 3H); 4.08 (q, 2H); 4.29 (s, 2H); 6.66 (dd, 1H); 6.73 (d, 1H); 7.14 (dd, 1H); 7.16 (d, 1H); 7.45 (m, 1H); 7.51 (dd, 1H); 8.86 (b, 1H, NH).

1f {2-Amino-4-[(benzo[b]thiophen-3-ylmethyl)-amino]-phenyl}-carbamic acid ethyl ester dihydrochloride Precipitation of the crude product from ethyl acetate by addition of ethereal hydrochloric acid gave the title compound.

M.p. 213-214° C. Calculated for C$_{18}$H$_{21}$N$_3$Cl$_2$O$_2$S: C, 51.68; H, 4.95; N, 10.05. Found: C, 51.88; H, 5.35; N, 9.95. LC/MS (m/z) 342.2 (M+H$^+$); $t_R$=2.08 min. $^1$H NMR (DMSO-d$_6$): 1.22 (t, 3H); 4.08 (q, 2H); 4.53 (s, 2H); 6.81 (dd, 1H); 6.93 (d, 1H); 7.19 (d, 1H); 7.41 (m, 2H); 7.70 (s, 1H); 7.98 (m, 2H); 8.97 (b, 1H, NH).

Example 2

2a (2-Amino-4-{[4-(4-chloro-benzenesulonyl)-3-methyl-thiophen-2-ylmethyl]-amino}-phenyl)-carbamic acid ethyl ester A suspension of 4-(4-chloro-benzenesulfonyl)-3-methyl-thiophene-2-carbaldehyde (301 mg, 1.00 mmol) and (4-amino-2-nitro-phenyl)-carbamic acid ethyl ester (293 mg, 1.30 mmol) in absolute ethanol (10 mL) was heated under reflux for 20 h under N$_2$. After cooling, the orange to red solid imine formed was collected by filtration and vacuum dried to yield a crude product (312 mg, 61%), which was suspended in methanol:acetic acid 10:1 (10 mL). NaBH$_3$CN (0.19 g, 3.0 mmol) was added and the mixture was stirred for 1 hour at room temperature. Then another portion of NaBH$_3$CN (0.19 g, 3.0 mmol) was added, and after further 1 hour, saturated aqueous sodium bicarbonate (20 mL) was added. The red solid amine formed was collected by filtration and vacuum dried to yield a crude product (293 mg, 94%) which was suspended in absolute ethanol (10 mL). To this was added 6 N HCl (1.1 mL, 6.6 mmol) and iron powder (193 mg, 3.46 mmol), and the red mixture was heated to 60° C. until the red color had faded to yellow, ca. 10-20 minutes. The mixture was poured into saturated aqueous sodium bicarbonate (50 mL) and EtOAc (50 mL), the resulting mixture was filtered, the phases were separated, and the aqueous phase was further extracted with EtOAc (2×50 mL). The combined organic phases were dried (Na$_2$SO$_4$) and the solvents evaporated in vacuo. The product was purified by chromatography on silica gel on a Flash-Master system using as eluent heptane/ethyl acetate (linear gradient elution, typically from 8:2 to 1:1). The fractions containing the product were pooled and evaporated in vacuo to yield the title compound as a pale yellow solid (213 mg, 78%). LC-MS: (m/z)=480.1 (M+H$^+$), calcd for C$_{21}$H$_{23}$ClN$_3$O$_4$S$_2$: 480.0813, t$_R$=2.35 min, UV purity=72.4%, ELS purity=86.5%. $^1$H NMR (DMSO-d$_6$): 1.19 (b, 3 H), 2.16 (s, 3 H), 4.02 (q, J=6.9 Hz, 2 H), 4.23 (d, J=6.1 Hz, 2 H), 4.57 (s, 2 H), 5.81 (dd, J=2.4, 8.5 Hz, 1 H), 5.91-5.95 (m, 2 H), 6.72 (broad d, J=6.6 Hz, 1 H), 7.72 (d, J=8.5 Hz, 2 H), 7.90 (d, J=8.5 Hz, 2 H), 8.15 (b, 1H), 8.31 (s, 1 H).

The following compounds were prepared analogously:

2b {2-Amino-4-[(3-chloro-thiophen-2-ylmethyl)-amino]-phenyl}-carbamic acid ethyl ester Yield: 76%. LC-MS: (m/z)=326.0 (M+H$^+$), calcd for C$_{14}$H$_{17}$ClN$_3$O$_2$S: 326.0725, t$_R$=1.95 min, UV purity=85.8%, ELS purity=98.1%. $^1$H NMR (DMSO-d$_6$): 1.19 (b, 3 H), 4.03 (q, J=7.1 Hz, 2 H), 4.30 (d, J=6.1 Hz, 2 H), 4.57 (s, 2 H), 5.83 (dd, J=2.4, 8.5 Hz, 1 H), 5.93-5.97 (m, 2 H), 6.73 (broad d, J=7.1 Hz, 1 H), 6.99 (d, J=5.2 Hz, 1 H), 7.48 (d, J=5.2 Hz, 1 H), 8.16 (b, 1 H).

2c {2-Amino-4-[(4bromo-3-methoxy-thiophen-2-ylmethyl)-amino]-phenyl}-carbamic acid ethyl ester Yield: 66%. LC-MS: (m/z)=402.0 (M+H$^+$), calcd for C$_{15}$H$_{19}$BrN$_3$O$_3$S: 400.0325 (100%), 402.0310 (97.3%), t$_R$=1.97 min, UV purity=87.9%, ELS purity=98.2%. $^1$H NMR (DMSO-d$_6$): 1.20 (b, 3 H), 3.83 (s, 3 H), 4.03 (q, J=6.9 Hz, 2 H), 4.32 (d, J=6.1 Hz, 2 H), 4.58 (s, 2 H), 5.84-5.89 (m, 2 H), 5.97 (d, J=2.4 Hz, 1 H), 6.74 (b, 1 H), 7.46 (s, 1 H), 8.17 (b, 1 H).

2d {2-Amino-4-[(6-chloro-3-methoxy-benzo[b]thiophen-2-ylmethyl)-amino]-phenyl}-carbamic acid ethyl ester Yield: 60%. LC-MS: (m/z)=405.3 (M+H$^+$), calcd for C$_{19}$H$_{21}$ClN$_3$O$_3$S: 406.0987, t$_R$=2.39 min, UV purity=95.0%, ELS purity=99.6%. $^1$H NMR (DMSO-d$_6$): 1.19 (b, 3 H), 3.95 (s, 3 H), 4.02 (q, J=7.1 Hz, 2 H), 4.43 (d, J=6.1 Hz, 2 H), 4.56 (s, 2 H), 5.90 (dd, J=2.4, 8.5 Hz, 1 H), 5.96 (t, J=5.9 Hz, 1 H), 6.00 (d, J=2.8 Hz, 1 H), 6.73 (broad d, J=6.6 Hz, 1 H), 7.39 (dd, J=1.9, 8.5 Hz, 1 H), 7.68 (d, J=8.5 Hz, 1 H), 7.98 (d, J=1.9 Hz, 1 H), 8.15 (b, 1H).

2e {2-Amino-4-[(5-dimethyl-amino-benzo[b]thiophen-3-ylmethyl)-amino]-phenyl}-carbamic acid ethyl ester Yield: 13%. LC-MS: (m/z)=385.0 (M+H$^+$), calcd for C$_{20}$H$_{25}$N$_4$O$_2$S: 385.1693, t$_R$=1.29 min, UV purity=87.8%, ELS purity=93.5%. $^1$H NMR (DMSO-d$_6$): 1.19 (b, 3 H), 2.94 (s, 6 H), 4.02 (q, J=6.9 Hz, 2 H), 4.34 (d, J=5.7 Hz, 2 H), 4.53 (s, 2 H), 5.81 (t, J=5.9 Hz, 1 H), 5.93 (dd, J=2.4, 8.5 Hz, 1 H), 6.03 (d, J=2.4 Hz, 1 H), 6.72 (b, 1 H), 6.95 (dd, J=2.4, 9.0 Hz, 1 H), 7.08 (d, J=2.4 Hz, 1 H), 7.38 (s, 1 H), 7.71 (d, J=8.5 Hz, 1 H), 8.15 (b, 1 H).

2f {2-Amino-4-[(5-dimethyl-amino-3-methyl-benzo[b]thiophen-2-ylmethyl)-amino]-phenyl}-carbamic acid ethyl ester Yield: 36%. LC-MS: (m/z)=399.2 (M+H$^+$), calcd for C$_{21}$H$_{27}$N$_4$O$_2$S: 399.1849, t$_R$=1.31 min, UV purity=98.4%, ELS purity=99.4%. $^1$H NMR (DMSO-d$_6$): 1.19 (b, 3 H), 2.33 (s, 3 H), 2.93 (s, 6 H), 4.02 (q, J=6.9 Hz, 2 H), 4.37 (d, J=5.7 Hz, 2 H), 4.54 (s, 2 H), 5.86 (dd, J=2.4, 8.5 Hz, 1 H), 5.89 (t, J=6.6 Hz, 1 H), 5.96 (d, J=2.4 Hz, 1 H), 6.71 (b, 1 H), 6.84-6.89 (m, 2 H), 7.58 (d, J=8.5 Hz, 1 H), 8.16 (b, 1 H).

Example 3

3a {2-Amino-4-[(5-methyl-thiophen-2-ylmethyl)-(methyl)-amino]-phenyl}-carbamic acid ethyl ester A mixture of 5-methyl-2-thiophenecarboxaldehyde (108 µL, 1.00 mmol), (4-amino-2-nitro-phenyl)-carbamic acid ethyl ester (225 mg, 1.00 mmol) and Amberlite IRC-84 (10 mg) in o-xylene (4 mL) was heated at reflux under Ar for 5 hours. Volatiles were removed by evaporation in vacuo, and the residue was dissolved in acetonitrile (5 mL). To the resulting solution was added NaBH$_3$CN (0.25 g, 4.0 mmol) followed by HOAc (5 drops). After stirring for 5 minutes, the solution became dark red. Formaldehyde (37% solution in water, 0.89 mL, 12 mmol) was added, and stiring was continued for 30 minutes with occasional addition of HOAc. The reaction mixture was evaporated to dryness in vacuo and the residue was partitioned between saturated aqueous sodium bicarbonate (50 mL) and EtOAc (50 mL). The aqueous phase was extracted with EtOAc (50 mL) and the combined organic layers were dried (Na$_2$SO$_4$) and the solvents evaporated in vacuo. The residue was then dissolved in ethanol (10 mL). 6 N aqueous HCl (2.0 mL, 12 mmol) and iron powder (0.34 g, 6.0 mmol) were added, and the red mixture was heated at 60° C. until the red color had faded to yellow, ca. 15 minutes. The mixture was poured into saturated aqueous sodium bicarbonate (50 mL) and EtOAc (50 mL), the resulting mixture was filtered, the phases were separated, and the aqueous phase was further extracted with EtOAc (2×50 mL). The combined organic layers were dried (Na$_2$SO$_4$) and the solvents evaporated in vacuo. The product was purified by chromatography on silica gel on a Flash-Master system using as eluent heptane/ethyl acetate (linear gradient elution, typically from 8:2 to 1:1). The fractions containing the product were pooled and evaporated in vacuo to yield the title compound as a pale yellow solid (145 mg, 45% overall). LC-MS: (m/z)=319.9 (M+H$^+$), calcd for C$_{16}$H$_{22}$N$_3$O$_2$S: 320.1427, t$_R$=1.80 min, UV purity=98.4%, ELS purity=97.2%. $^1$H NMR (CDCl$_3$): 1.29 (t, J=7.1, 3 H), 2.41 (s, 3 H), 2.91 (s, 3 H), 3.76 (b, 2 H), 4.19 (q, J=7.1 Hz, 2 H), 4.52 (s, 2 H), 6.02 (b, 1 H), 6.17 (d, J=2.8 Hz, 1 H), 6.25 (dd, J=2.8, 8.5 Hz, 1 H), 6.53-6.58 (m, 1 H), 6.66 (d, J=3.3 Hz, 1 H), 6.98 (d, J=8.5 Hz, 1 H).

The following compound was prepared analogously:

3b {2-Amino-4-[(5-chloro-thiophen-2-ylmethyl)-(methyl)-amino]-phenyl}-carbamic acid ethyl ester Yield: 34%. LC-MS: (m/z)=340.0 (M+H$^+$), calcd for C$_{15}$H$_{19}$ClN$_3$O$_2$S: 340.0881, t$_R$=2.14 min, UV purity=82.3%, ELS purity=90.2%. $^1$H NMR (CDCl$_3$): 1.29 (t, J=6.8, 3 H), 2.91 (s, 3 H), 3.78 (b, 2 H), 4.20 (q, J=7.2 Hz, 2 H), 4.49 (s, 2 H), 6.05 (b, 1 H), 6.16 (d, J=2.4 Hz, 1 H), 6.24 (dd, J=2.4, 8.5 Hz, 1 H), 6.73 (d, J=3.8 Hz, 1 H), 6.99 (d, J=8.5 Hz, 1 H).

The following compound was prepared analogously, except that formaldehyde was substituted for acetaldehyde:

3c {2-Amino-4-[(5-chloro-thiophen-2-ylmethyl)-(ethyl)-amino]-phenyl}-carbamic acid ethyl ester Yield: 12%. LC-MS: (m/z)=353.9 (M+H$^+$), calcd for C$_{16}$H$_{21}$ClN$_3$O$_2$S: 354.1038, $t_R$=2.02 min, UV purity=97.5%, ELS purity=99.0%. $^1$H NMR (CDCl$_3$): 1.16 (t, J=7.1, 3 H), 1.29 (t, J=6.8, 3 H), 3.36 (q, J=7.1 Hz, 2 H), 3.76 (b, 2 H), 4.19 (q, J=7.2 Hz, 2 H), 4.47 (s, 2 H), 6.05 (b, 1 H), 6.13 (d, J=2.4 Hz, 1 H), 6.19 (dd, J=2.4, 9.0 Hz, 1 H), 6.73 (d, J=3.8 Hz, 1 H), 6.96 (d, J=8.0 Hz, 1 H).

The following compound was prepared analogously, except that the formaldehyde addition was omitted:

3d {2-Amino-4-[(5-fluoro-thiophen-2-ylmethyl)-amino]-phenyl}-carbamic acid ethyl ester Yield: 65% (25% after prep. LC-MS purification to remove non-fluorinated by-product). LC-MS: (m/z)=310.2 (M+H$^+$), calcd for C$_{14}$H$_{17}$FN$_3$O$_2$S: 310.1020, $t_R$=1.76 min, UV purity=96.6%, ELS purity=83.4%. $^1$H NMR (CDCl$_3$): 1.29 (b, 3 H), 3.82 (b, 2 H), 4.19 (q, J=7.2 Hz, 2 H), 4.31 (d, J=2.0 Hz, 2 H), 6.05 (b, 1 H), 6.09 (d, J=8.0 Hz, 1 H), 6.29 (dd, J=1.5, 3.8 Hz, 1 H), 6.58 (t, J=3.5 Hz, 1 H), 6.94 (d, J=8.0 Hz, 1 H).

Example 4

4a {2-Amino-4-[(5-chloro-thiophen-2-ylmethyl)-amino]-phenyl}-carbamic acid ethyl ester A solution of 5-chlorothiophene-2-carbaldehyde (240 μL, 111 μmol, 463 mM in 1,2-dichloroethane) was added to a solution of 4-amino-2-nitrophenylcarbamic acid ethyl ester (240 μL, 111 μmol, 463 mM in 1,2-dichloroethane). Sodium triacetoxyborohydride (118 mg, 555 μmol) was added, and the resulting mixture was stirred for 3.5 hours at 40° C. The mixture was allowed to cool to ambient temperature, and water (100 μL) was added. The mixture was filtered through silica gel (500 mg) and the column was washed with 1,2-dichloroethane (3 mL). The combined organic phases were evaporated to dryness in vacuo. The resulting solid was dissolved in ethanol (3 mL). Iron (19 mg) was added to one-third of the resulting solution (1 mL), followed by an aqueous solution of hydrochloric acid (96 μL, 6M). The resulting mixture was placed in an ultrasonic bath for 10 minutes. Then, saturated aqueous sodium bicarbonate solution (2 mL) was added. The mixture was extracted with ethyl acetate (3 mL). The organic phase was washed with water (3 mL) and brine (3 mL), dried over magnesium sulphate, filtered, and evaporated to dryness in vacuo. The resulting product was dissolved in 190 μL dimethylsulfoxide and subjected to preparative LC-MS purification. The resulting solution was evaporated to dryness in vacuo. Yield (6.8 mg, 56%). LC-MS (m/z) (M+H)$^+$ 326.1 RT=1.90 (UV, ELSD) 92%, 99%.

The following compounds were prepared in an analogous fashion:

4b {2-Amino-4-[(5-bromo-thiophen-2-ylmethyl)-amino]-phenyl}-carbamic acid ethyl ester LC-MS (m/z) (M+H)$^+$ 371.9 RT=1.94 (UV, ELSD) 89%, 98%.

4c {2-Amino-4-[(4-bromo-thiophen-2-ylmethyl)-amino]-phenyl}-carbamic acid ethyl ester LC-MS (m/z) (M+H)$^+$ 372.0 RT=1.96 (UV, ELSD) 76%, 100%.

4d {2-Amino-4-[(5-ethyl-thiophen-2-ylmethyl)-amino]-phenyl}-carbamic acid ethyl ester LC-MS (m/z) (M+H)$^+$ 320.1 RT=1.90 (UV, ELSD) 72%, 96%.

4e {2-Amino-4-[(benzo[b]thiophen-2-ylmethyl)-amino]-phenyl}-carbamic acid ethyl ester LC-MS (m/z) (M+H)$^+$ 342.1 RT=2.06 (UV, ELSD) 75%, 100%.

4f {2-Amino-4-[(5-phenyl-thiophen-2-ylmethyl)-amino]-phenyl}-carbamic acid ethyl ester LC-MS (m/z) (M+H)$^+$ 368.2 RT=2.21 (UV, ELSD) 90%, 99%.

Example 5

5a {2-Amino-4-[(benzo[b]thiophen-2-ylmethyl)-amino]-phenyl}-carbamic acid propyl ester Benzo[b]thiophene-2-carbaldehyde (1.36 g, 8.38 mmol) was added to a solution of (4-amino-2-nitro-phenyl)-carbamic acid propyl ester (2.00 g, 8.36 mmol) in acetonitrile (10 mL). The mixture was heated to 160° C. for 2 minutes in a 20 mL sealed microwave process vial. Upon cooling NaBH$_3$CN (1.06 g, 16.7 mmol) and AcOH (48 μL, 0.84 mmol) were added and the mixture was stirred for 30 minutes at 25° C. Water/brine (1:1, 100 mL) was added and the mixture was extracted with ethyl acetate (3×100 mL). The organic phase was dried over magnesium sulphate, filtered and concentrated in vacuo. The crude intermediate was purified by flash chromatography on silica gel (eluent: ethyl acetate:heptane 1:9), and evaporated to dryness. The intermediate was then dissolved in tetrahydrofuran (20 mL) and Na$_2$S$_2$O$_4$ (3.67 g, 21 mmol) dissolved in water (50 mL) was added. The resulting mixture was stirred at 40° C. for 5 hours under argon. The resulting mixture was extracted with ethyl acetate (3×100 mL), the combined organic phases dried over magnesium sulphate, filtered, and concentrated in vacuo. Purification by flash chromatography (eluent: ethyl acetate:heptane 1:1) furnished 0.3 g (10%) of the title compound as a solid. LC/MS (m/z) 356 ([M+H]$^+$); RT=2.45 min. $^1$H NMR (CDCl$_3$): 0.95 (t, 3H); 1.67 (m, 2H); 4.08 (t, 2H); 4.55 (s, 2H); 6.08 (d, 1H); 6.13 (dd, 1H); 6.93 (d, 1H); 7.20 (s, 1H); 7.27 (dt, 1H); 7.32 (dt, 1H); 7.68 (d, 1H); 7.77 (d, 1H).

The following compound was prepared in an analogous fashion:

5b {2-Amino4-[(benzo[b]thiophen-3-ylmethyl)-amino]-phenyl}-carbamic acid propyl ester Yield: 16%. LC/MS (m/z) 356 ([M+H]$^+$); RT=2.24 min. $^1$H NMR (CDCl$_3$): 0.96 (t, 3H); 1.68 (m, 2H); 4.10 (t, 2H); 4.51 (s, 2H); 6.12 (d, 1H); 6.14 (dd, 1H); 6.95 (d, 1H); 7.36 (s, 1H); 7.39 (dt, 1H); 7.40 (dt, 1H); 7.79 (dd, 1H); 7.87 (dd, 1H).

Example 6

6a N-{2-Amino-4-[(5-chlorothiophen-2-ylmethyl) amino]phenyl}-2-(4-fluorophenyl)-acetamide To a stirred red solution of N-{4-[(5-chlorothiophen-2-ylmethyl)amino]-2-nitrophenyl}-2-(4-fluorophenyl)acetamide (320 mg, 0.762 mmol) in tetrahydrofuran (25 ml) and acetic acid (8 mL) zinc powder (particle size <10 micron, 10 g) was periodically added by portions during 30 minutes. The solution turned colorless after 5 minutes. The obtained colorless suspension was filtered via plug of $SiO_2$ (10 g) with ethyl acetate as an eluent and the obtained solution was evaporated in vacuo. The obtained solid was dissolved in a mixture of ethyl acetate/acetone/trifluoroacetic (3 mL/3 mL/0.2 mL), treated with saturated aq. $NaHCO_3$ (50 mL) and heptane (30 mL) and the product was separated by filtration to furnish 280 mg of a pale grey solid. Yield 94.2%. LC/MS (m/z) 390.4 ([M+H]$^+$); RT=2.26 (UV, ELSD) 99%, 100%. $^1$H NMR (DMSO-d$_6$): 3.56 (s, 2H); 4.28 (d, 2H); 4.57 (s, 2H, NH$_2$); 5.87 (dd, 1H); 5.98 (m, 2H, NH and arom. H); 6.74 (d, 1H); 6.86 (d, 1H); 6.93 (d, 1H); 7.13 (t, 2H); 7.35 (dd, 2H); 9.10 (s, 1H).

The following compound was prepared analogously from the corresponding nitro compound:

6b N-{2-Amino-4-[(5-chlorothiophen-2-ylmethyl) amino]phenyl}-3,3-dimethylbutyramide After filtration through $SiO_2$ and evaporation the product was precipitated from a biphasic solution in ethyl acetate—saturated aq. $NaHCO_3$ (5 mL/20 mL) with heptane (50 mL). Yield 580 mg, 71.5%. LC/MS (m/z) 352.48 ([M+H]$^+$); RT=2.16 (UV, ELSD) 96%, 99%. $^1$H NMR (DMSO-d$_6$): 1.01 (s, 9H), 2.11 (s, 2H); 4.29 (d, 2H); 4.54 (s, 2H, NH$_2$); 5.88 (dd, 1H); 5.97 (t, 1H, NH); 5.99 (d, 1H); 6.72 (d, 1H); 6.87 (d, 1H); 6.93 (d, 1H); 8.82 (s, 1H).

In Vitro and In Vivo Testing

The compounds of the invention have been tested and shown effect in one or more of the below models:

Relative Efflux Through the KCNQ2 Channel

Cells stably expressing voltage-gated KCNQ2 channels were seeded on the day before the experiment and loaded with [$^{86}$Rb]. On the day of the experiment cells were washed with a HBSS-containing buffer. Cells were preincubated with drug and the [$^{86}$Rb+] was stimulated by a submaximal concentration of 15 mM KCl in the continued presence of drug. After a suitable incubation period, the supernatant was removed and counted in a liquid scintillation counter (Tricarb). Cells were lysed with 2 mM NaOH and the amount of $^{86}$Rb+ was counted. The relative efflux was calculated (($CPM_{suoer}/CPM_{super}+CPM_{cell})_{Cmpd}/(CPM_{suoer}/CPM_{super}+CPM_{cell})_{15\ mM\ KCl})*100-100$.

The compounds of the invention have an $EC_{50}$ of less than 20000 nM, in most cases less than 200 nM and in many cases less than 200 nM. Accordingly, the compounds of the invention are considered to be useful in the treatment of diseases associated with the KCNQ family potassium channels.

Maximum Electroshock

The test was conducted in groups of male mice using corneal electrodes and administering a square wave current of 26 mA for 0.4 seconds in order to induce a convulsion characterised by a tonic hind limb extension (Wlaz et al. *Epilepsy Research* 1998, 30, 219-229).

Pilocarpine Induced Seizures

Pilocarpine induced seizures are induced by intraperitoneal injection of pilocarpine 250 mg/kg to groups of male mice and observing for seizure activity resulting in loss of posture within a period of 30 minutes (Starr et al. *Pharmacology Biochemistry and Behavior* 1993, 45, 321-325)

Electrical Seizure—Threshold Test

A modification of the up-and-down method (Kimball et a., *Radiation Research* 1957, 1-12) was used to determine the median threshold to induce tonic hind-limb extension in response to corneal electroshock in groups of male mice. The first mouse of each group received an electroshock at 14 mA, (0.4 s, 50 Hz) and was observed for seizure activity. If a seizure was observed the current was reduced by 1 mA for the next mouse, however, if no seizure was observed then the current was increased by 1 mA. This procedure was repeated for all 15 mice in the treatment group.

Chemical Seizure—Threshold Test

The threshold dose of pentylenetetrazole required to induce a clonic convulsion was measured by timed infusion of pentylenetetrazole (5 mg/mL at 0.5 mL/min) into a lateral tail vein of groups of male mice (Nutt et al. *J Pharmacy and Pharmacology* 1986, 38, 697-698).

Amygdala Kindling

Rats underwent surgery to implantation of tri-polar electrodes into the dorsolateral amygdala. After surgery the animals were allowed to recover before the groups of rats received either varying doses of test compound or the drug's vehicle. The animals were stimulated with their initial after discharge threshold +25 µA daily for 3-5 weeks and on each occasion seizure severity, seizure duration, and duration of electrical after discharge were noted. (Racine. *Electroencephalography and Clinical Neurophysiology* 1972, 32, 281-294)

Side Effects

Central nervous system side-effects were measured by measuring the time mice would remain on rotarod apparatus (Capacio et al. *Drug and Chemical Toxicology* 1992, 15, 177-201); or by measuring their locomotor activity by counting the number of infra-red beams crossed in a test cage ((Watson et al. *Neuropharinacology* 1997, 36, 1369-1375). Hypothermic actions on the animals core body temperature of the compound were measured by either rectal probe or implanted radiotelemetry transmitters capable of measuring temperature (Keeney et al. *Physiology and Behaviour* 2001, 74, 177-184.

Pharmacokinetics

The pharmacokinetic properties of the compound were determined via. i.v. and p.o. dosing to Spraque Dawley rats, and, thereafter, drawing blood samples over 20 hours. Plasma concentrations were determined with LC/MS/MS.

The invention claimed is:

1. A 1,2,4-triaminobenzene derivative of formula I:

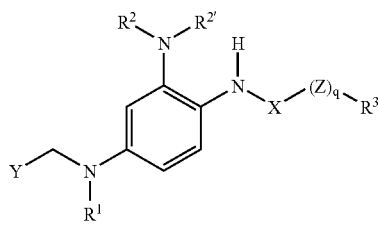

wherein:
- $R^1$ is selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, acyl, hydroxy-$C_{1-6}$-alk(en/yn)yl and hydroxy-$C_{3-8}$-cycloalk(en)yl;
- $R^2$ and $R^{2'}$ are independently selected from the group consisting of hydrogen, $C_{1-6}$-alk(en/yn)yl, $C_{3-8}$-cycloalk(en)yl, aryl, $C_{3-8}$-cycloalk(en)yl-$C_{1-6}$-alk(en/yn)yl, aryl-$C_{1-6}$-alk(en/yn)yl, acyl, hydroxy-$C_{1-6}$-alk(en/yn)yl and hydroxy-$C_{3-8}$-cycloalk(en)yl;
- $R^3$ is selected from the group consisting of hydrogen, $C_{1-6}$-alk(en/yn)yl, $C_{3-8}$-cycloalk(en)yl, aryl, $C_{3-8}$-cycloalk(en)yl-$C_{1-6}$-alk(en/yn)yl, aryl-$C_{1-6}$-alk(en/yn)yl, hydroxy-$C_{1-6}$-alk(en/yn)yl, aryl-$C_{3-8}$-cycloalk(en)yl, $NR^{10}R^{10'}$—$C_{1-6}$-alk(en/yn)yl, $NR^{10}R^{10'}$—$C_{3-8}$-cycloalk(en)yl and hydroxy-$C_{3-8}$-cycloalk(en)yl, wherein:
  - $R^{10}$ and $R^{10'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano-$C_{1-6}$-alk(en/yn)yl, cyano-$C_{3-8}$-cycloalk(en)yl and cyano-$C_{3-8}$-cycloalk(en)yl-$C_{1-6}$-alk(en/yn)yl, or
  - $R^{10}$ and $R^{10'}$ together with the nitrogen atom to which they are attached form a 4-8 membered saturated or unsaturated ring that optionally contains 1, 2 or 3 further heteroatoms;
- X is CO or $SO_2$;
- Z is O or $NR^4$, wherein:
  - $R^4$ is selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, hydroxy-$C_{1-6}$-alk(en/yn)yl and hydroxy-$C_{3-8}$-cycloalk(en)yl; or
  - $R^3$ and $R^4$ together with the nitrogen atom to which they are attached form a 4-8 membered saturated or unsaturated ring that optionally contains 1, 2 or 3 further heteroatoms, the ring formed by $R^3$ and $R^4$ and the nitrogen atom is optionally substituted with one or more substituents independently selected from $C_{1-6}$-alk(en/yn)yl, aryl and aryl-$C_{1-6}$-alk(en/yn)yl;
- q is 0 or 1; and Y represents a heteroaryl of formula II:

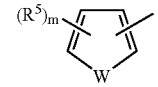

wherein:
- W is S;
- m is 0, 1, 2 or 3;
- n is 0, 1, 2, 3 or 4;
- p is 0 or 1; and
- each $R^5$ is independently selected from the group consisting of $C_{1-6}$-alk(en/yn)yl, $C_{3-8}$-cycloalk(en)yl, aryl, $C_{3-8}$-cycloalk(en)yl-$C_{1-6}$-alk(en/yn)yl, aryl-$C_{1-6}$-alk(en/yn)yl, acyl, halogen, halo-$C_{1-6}$-alk(en/yn)yl, $C_{1-6}$-alk(en/yn)yloxy, —CO—$NR^6R^{6'}$, cyano, nitro, —$NR^7R^{7'}$, —S—$R^8$, —$SO_2R^8$, and $SO_2OR^8$, wherein:
  - $R^6$ and $R^{6'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl and aryl;
  - $R^7$ and $R^{7'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, aryl and acyl; and
  - $R^8$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, aryl and —$NR^9R^{9'}$, wherein:
    - $R^9$ and $R^{9'}$ are independently selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl;

or a pharmaceutically acceptable salt thereof.

2. The compound according to claim 1 wherein $R^1$ is selected from the group consisting of hydrogen and $C_{1-6}$-alk(en/yn)yl.

3. The compound according to claim 1 wherein at least one of the substituents $R^2$ and $R^{2'}$ is a hydrogen atom.

4. The compound according to claim 1 wherein both $R^2$ and $R^{2'}$ are hydrogen atoms.

5. The compound according to claim 1 wherein X is CO.

6. The compound according to claim 1 wherein q is 0.

7. The compound according to claim 1 wherein q is 1 and Z is an oxygen atom.

8. The compound according to claim 1 wherein $R^3$ is selected from the group consisting of $C_{1-6}$-alk(en/yn)yl and aryl-$C_{1-6}$-alk(en/yn)yl.

9. The compound according to claim 8 wherein $R^3$ is $C_{1-6}$-alk(en/yn)yl.

10. The compound according to claim 8 wherein $R^3$ is aryl-$C_{1-6}$-alk(en/yn)yl.

11. The compound according to claim 1 wherein W is a sulfur atom.

12. The compound according to claim 1 wherein Y is of formula IIb:

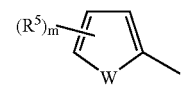

wherein W, m, n, p and $R^5$ are as defined in claim 1.

13. The compound according to claim 1 wherein Y is of formula IIc:

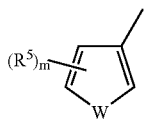

wherein W, m, n, p and $R^5$ are as defined in claim 1.

14. The compound according to claim 1 wherein each $R^5$ is independently selected from the group consisting of $C_{1-6}$-alk(en/yn)yl, aryl, halogen, $C_{1-6}$-alk(en/yn)yloxy, —$NR^7R^{7'}$, and —$SO_2R^8$.

15. A compound selected from the group consisting of:
{2-Amino-4-[(5-chloro-thiophen-2-ylmethyl)-methyl-amino]-phenyl}-carbamic acid ethyl ester;
{2-Amino-4-[(5-chloro-thiophen-2-ylmethyl)-amino]-phenyl}-carbamic acid ethyl ester;
{2-Amino-4-[(5-methyl-thiophen-2-ylmethyl)-methyl-amino]-phenyl}-carbamic acid ethyl ester;
{2-Amino-4-[(5-bromo-thiophen-2-ylmethyl)-amino]-phenyl}-carbamic acid ethyl ester;
{2-Amino-4-[(5-methyl-thiophen-2-ylmethyl)-amino]-phenyl}-carbamic acid ethyl ester;
{2-Amino-4-[(4-bromo-3-methoxy-thiophen-2-ylmethyl)-amino]-phenyl}-carbamic acid ethyl ester;
{2-Amino-4-[(5-phenyl-thiophen-2-ylmethyl)-amino]-phenyl}-carbamic acid ethyl ester;
{2-Amino-4-[(3-chloro-thiophen-2-ylmethyl)-amino]-phenyl}-carbamic acid ethyl ester;
(2-Amino-4-{[4-(4-chloro-benzenesulfonyl)-3-methyl-thiophen-2-ylmethyl]-amino}-phenyl)-carbamic acid ethyl ester;
{2-Amino-4-[(3-methyl-thiophen-2-ylmethyl)-amino]-phenyl}-carbamic acid ethyl ester;
{2-Amino-4-[(thiophen-2-ylmethyl)-amino]-phenyl}-carbamic acid ethyl ester;
{2-Amino-4-[(4-bromo-thiophen-2-ylmethyl)-amino]-phenyl}-carbamic acid ethyl ester;
{2-Amino-4-[(5-ethyl-thiophen-2-ylmethyl)-amino]-phenyl}-carbamic acid ethyl ester;
{2-Amino-4-[(thiophen-3-ylmethyl)-amino]-phenyl}-carbamic acid ethyl ester;
{2-Amino-4-[(5-chloro-thiophen-2-ylmethyl)-ethyl-amino]-phenyl}-carbamic acid ethyl ester;
{2-Amino-4-[(5-fluoro-thiophen-2-ylmethyl)-amino]-phenyl}-carbamic acid ethyl ester;
N-{2-Amino-4-[(5-chloro-thiophen-2-ylmethyl)amino]phenyl}-2-(4-fluoro-phenyl)-acetamide; and
N-{2-Amino-4-[(5-chloro-thiophen-2-ylmethyl)amino]phenyl}-3,3-dimethyl-butyramide;
or a pharmaceutically acceptable salt thereof.

16. A pharmaceutical composition comprising a compound according to claim 1 together with one or more pharmaceutically acceptable carriers or diluents.

17. A method of treating a disorder of the central nervous system in a subject, wherein the disorder of the central nervous system is selected from the group consisting of a seizure, neuropathic pain, migraine pain, and anxiety, comprising administering a therapeutically effective amount of the compound of claim 1 to the subject.

18. The method of claim 17, wherein the seizure is a convulsion, an epilepsy or a status epilepticus.

19. The method of claim 17, wherein the neuropathic pain is allodynia, hyperalgesic pain, phantom pain, neuropathic pain related to diabetic neuropathy or neuropathic pain related to migraine.

20. The method of claim 17, wherein the anxiety is a generalized anxiety-disorder, panic anxiety, an obsessive compulsive disorder, social phobia, performance anxiety, post-traumatic stress disorder, an acute stress reaction, an adjustment disorder, a hypochondriacal disorder, a separation anxiety disorder, agoraphobia, a specific phobia, an anxiety disorder due to a general medical condition or a substance-induced anxiety disorder.

* * * * *